US011422132B2

(12) United States Patent
Fairclough et al.

(10) Patent No.: US 11,422,132 B2
(45) Date of Patent: Aug. 23, 2022

(54) PEPTIDES AND USES THEREOF FOR DIAGNOSING AND TREATING MYASTHENIA GRAVIS

(71) Applicant: The Regents of the University of California, Oakland, CA (US)

(72) Inventors: Robert H. Fairclough, Davis, CA (US); Vu B. Trinh, Pittsburg, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/294,820

(22) Filed: Mar. 6, 2019

(65) Prior Publication Data

US 2020/0033338 A1 Jan. 30, 2020

Related U.S. Application Data

(63) Continuation of application No. PCT/US2017/050521, filed on Sep. 7, 2017.

(60) Provisional application No. 62/384,896, filed on Sep. 8, 2016.

(51) Int. Cl.

| | |
|---|---|
| ***G01N 33/564*** | (2006.01) |
| ***A61K 47/68*** | (2017.01) |
| ***C07K 14/47*** | (2006.01) |
| ***G01N 33/68*** | (2006.01) |
| ***A61K 38/00*** | (2006.01) |

(52) U.S. Cl.

CPC ....... *G01N 33/564* (2013.01); *A61K 47/6849* (2017.08); *C07K 14/47* (2013.01); *G01N 33/6857* (2013.01); *A61K 38/00* (2013.01); *G01N 2800/10* (2013.01); *G01N 2800/2835* (2013.01)

(58) Field of Classification Search

None

See application file for complete search history.

(56) References Cited

U.S. PATENT DOCUMENTS

2007/0269865 A1* 11/2007 Fuchs ................ A61K 39/0008 435/69.1

FOREIGN PATENT DOCUMENTS

| | | | |
|---|---|---|---|
| JP | H06-211895 | A | 8/1994 |
| JP | 2003-509045 | A | 3/2003 |
| JP | 2007-183176 | A | 7/2007 |
| JP | 2011-032188 | A | 2/2011 |
| WO | 2018/049053 | A2 | 3/2018 |

OTHER PUBLICATIONS

The website downloaded on Apr. 22, 2020 from https://www.mayoclinic.org/diseases-conditions/myasthenia-gravis/diagnosis-treatment/drc-20352040?p=1; 6 pages total (Year: 2020).*

Bhattacharya et al., PLoS ONE 12(3): e0171355. https://doi.org/10.1371/journal.pone.0171355; 22 pages total (Year: 2017).*

Matthew N. Meriggoli and Donald B. Sanders, Author Manuscript of Expert Rev Clin Immunol. Jul. 2012; 8(5): 427-438; 22 pages total (Year: 2012).*

Barchan et al., Modulation of the Anti-Acetylcholine Receptor Response and Experimental Autoimmune Myasthenia Gravis by Recombinant Fragments of the Acetylcholine Receptor, Eur. J. Immunol., vol. 28, No. 2, Feb. 1998, pp. 616-624.

Beroukhim et al., Three-Dimensional Location of the Main Immunogenic Region of the Acetylcholine Receptor, Neuron, vol. 15, No. 2, Aug. 1995, pp. 323-331.

Boulter et al., Isolation of a Clone Coding for the alpha-Subunit of a Mouse Acetylcholine Receptor, Molecular Neurobiology Laboratory, vol. 5, No. 9, Sep. 1985, pp. 2545-2552.

Conti-Tronconi et al., Monoclonal Antibodies as Probes of Acetylcholine Receptor Structure. 2. Binding to Native Receptor, Biochemistry, vol. 20, No. 8, Apr. 14, 1981, pp. 2181-2191.

Fostieri et al., The Conformation of the Main Immunogenic Region on the Alpha-Subunit of Muscle Acetylcholine Receptor is Affected by Neighboring Receptor Subunits, FEBS Letters, vol. 481, No. 2, Sep. 15, 2000, pp. 127-130.

Gomez et al., Monoclonal Anti-Acetylcholine Receptor Antibodies with Differing Capacities to Induce Experimental Autoimmune Myasthenia Gravis, J. Immunol., vol. 135, No. 1, Jul. 1985, pp. 232-241.

Gomez et al., Monoclonal Hybridoma Anti-Acetylcholine Receptor Antibodies: Antibody Specificity and Effect of Passive Transfer, Ann N Y Acad. Sci., vol. 377, Dec. 1981, pp. 97-109.

Lindstrom, J. M., Acetylcholine Receptors and Myasthenia, Muscle Nerve, vol. 23, No. 4, Apr. 2000, pp. 453-477.

Lindstrom et al., Pathological Mechanisms in Experimental Autoimmune Myasthenia Gravis, The Journal of Experimental Medicine, vol. 144, No. 3, Sep. 1, 1976, pp. 739-753.

Morell et al., Structural Characterization of the Main Immunogenic Region of the Torpedo Acetylcholine Receptor, Molecular Immunology, vol. 58, No. 1, Mar. 2014, pp. 116-131.

Papadouli et al., Antigenic Role of Single Residues within the Main Immunogenic Region of the Nicotinic Acetylcholine Receptor, Biochem., J., vol. 269, No. 1, Jul. 1, 1990, pp. 239-245.

(Continued)

*Primary Examiner* — Christina M Borgeest

(74) *Attorney, Agent, or Firm* — Kilpatrick Townsend & Stockton LLP

(57) ABSTRACT

The invention provides compositions and methods for detecting or determining the severity of myasthenia gravis in a subject. The invention also provides compositions and methods for preventing or treating myasthenia gravis in a subject. In some embodiments, the compositions are peptides that bind to monoclonal antibodies that bind to the main immunogenic region of an acetylcholine receptor, and in some instances block pathogenic antibody combining sites. In other embodiments, the peptides further comprise an antibody heavy chain fragment. Kits for detecting or determining the severity of and preventing or treating myasthenia gravis are also provided.

22 Claims, 14 Drawing Sheets

Specification includes a Sequence Listing.

(56) References Cited

OTHER PUBLICATIONS

Richman et al., Effector Mechanisms of Myasthenic Antibodies, Ann N Y Acad. Sci., vol. 681, Jun. 21, 1993, pp. 264-273.
Richman et al., Monoclonal Anti-Acetylcholine Receptor Antibodies can cause Experimental Myasthenia, Nature, vol. 286, Aug. 1980, pp. 738-739.
Trinh et al., Therapeutic Peptide Mimics of the Acetylcholine Receptor Main Immunogenic Region For Treating Myasthenia Gravis, Ph.D. Thesis, University of California, Davis, ProQuest Dissertations Publishing 2013, retrieved on Mar. 6, 2018, 225 pages.
Trinh et al., Design, Synthesis, and Characterization of a 39 Amino Acid Peptide mimic of the Main Immunogenic Region of the Torpedo Acetylcholine Receptor, Molecular Immunology, vol. 5, Issue 1, May 2014, pp. 79-90.
Tzartos et al., Localization of the Main Immunogenic Region of Human Muscle Acetylcholine Receptor to Residues 67-76 of the alpha Subunit, Proc. Natl. Acad., vol. 85, May 1988, pp. 2899-2903.
Tzartos et al., Main Immunogenic Region of Torpedo Electroplax and Human Muscle Acetylcholine Receptor: Localization and Microheterogeneity Revealed by the Use of Synthetic Peptides, Journal of Neurochemistry, vol. 54, No. 1, Jan. 1990, pp. 51-61.
Tzartos et al., Mapping of Surface Structures of Electrophorus Acetylcholine Using Monoclonal Antibodies, The Journal of Biological Chemistry, vol. 256, No. 16, Aug. 25, 1981, pp. 8635-8645.
Tzartos et al., Monoclonal antibodies used to probe acetylcholine receptor structure: Localization of the main immunogenic region and detection of similarities between subunits, Proc. Natl. Acad. Sci., vol. 77, No. 2, Feb. 1980, pp. 755-759.
Tzartos et al., Passive Transfer of Experimental Autoimmune Myasthenia Gravis by Monoclonal Antibodies to the Main Immunogenic Region of the Acetylcholine Receptor, Journal of Neuroimmunology, vol. 15, No. 2, Jun. 1987, pp. 185-194.
Tzartos et al., Specificities of Antibodies to Acetylcholine Receptors in Sera from Myasthenia Gravis Patients Measured by Monoclonal Antibodies, Proc. Natl. Acad., vol. 79, Jan. 1982, pp. 188-192.
Unwin, N., Refined Structure of the Nicotinic Acetylcholine Receptor at 4Å Resolution, J. Mol. Biol., vol. 346, No. 4, Mar. 4, 2005, pp. 967-989.
Venkatesh et al., Prevention of Passively Transferred Experimental Autoimmune Myasthenia Gravis by a Phage Library-Derived Cyclic Peptide, PNAS, vol. 97, No. 2, Jan. 18, 2000, pp. 761-766.
Extended European Search Report in EP Application 17849543.8 dated Feb. 14, 2020; 10 pages.
Luo, J. et al.; "Main Immunogenic Region Structure Promotes Binding of Conformation-Dependent Myasthenia Gravis Autoantibodies, Nicotinic Acetylcholine Receptor Conformation Maturation, and Agonist Sensitivity"; The Journal of Neuroscience; vol. 29, No. 44; Nov. 4, 2009; pp. 13898-13908.
Japanese Office Action for JP Appl. No. JP019-513015 dated Aug. 4, 2021, 8 pages.

* cited by examiner

FIG. 2

| | | |
|---|---|---|
| 1 12 65 79 110 115 | | |
| SEHETRLVANLLGGGSLRWNPADYGGIKKIRGSLDYTGK | *Torpedo* | |
| SEHETRLVAKLFGGGSLKWNPDDYGGVKKIHGSLDYTGH | mouse | |
| SEHETRLVAKLFGGGSLKWNPDDYGGVKKIHGSLQYTGH | human | |

FIG. 4

| 1 12 65 79 110 115 | |
|---|---|
| SEHETRLVANLLGGGSLRWNPADYGGIKKIRGSLDYTGK | *Torpedo* |
| SEHETRLVAKLFGGGSLKWNPDDYGGVKKIHGSLQYTGH | human |
| SEHETRLVAKLLGGGSLRWNPADYGGIKKIRGSLDYTGK | N10K |
| SEHETRLVANLFGGGSLRWNPADYGGIKKIRGSLDYTGK | L12F |
| SEHETRLVANLLGGGSLRWNPADYGGIKKIRGSLDYTGK | R66K |
| SEHETRLVANLLGGGSLRWNPDDYGGIKKIRGSLDYTGK | A70D |
| SEHETRLVANLLGGGSLRWNPADYGGVKKIRGSLDYTGK | I75V |
| SEHETRLVANLLGGGSLRWNPADYGGIKKIHGSLDYTGK | R79H |
| SEHETRLVANLLGGGSLRWNPADYGGIKKIRGSLQYTGK | D111Q |
| SEHETRLVANLLGGGSLRWNPADYGGIKKIRGSLDYTGH | K115H |

```
1          12    65              79  110  115

SEHETRLVAKLFGGGSLKWNPDDYGGVKKIHGSLQYTGH    human
SEHETRLVANLFGGGSLKWNPDDYGGVKKIHGSLQYTGH    K10N
SEHETRLVAKLFGGGSLKWNPADYGGVKKIHGSLQYTGH    D70A
SEHETRLVAKLFGGGSLKWNPDDYGGIKKIHGSLQYTGH    V75I
SEHETRLVAKLFGGGSLKWNPDDYGGVKKIHGSLDYTGH    Q111D
```

| | Normal 3A | Normal 7 | Normal 10 | MG Sera 82 | MG Sera 86 | MG Sera 87 | MG Sera 91 | MG Sera 89 | MG Sera 90 | MG Sera 92 | MG Sera 93 |
|---|---|---|---|---|---|---|---|---|---|---|---|
| Torpedo 3MIR | | | | | | | | | | | |
| Human 3MIR | | | | | | | | | | | |
| K105/V75/ Q111D mutant | | | | | | | | | | | |
| K105/D78/ V75/Q111D mutant | | | | | ● | | ● | ● | ● | ● | ● |

PEPTIDES AND USES THEREOF FOR DIAGNOSING AND TREATING MYASTHENIA GRAVIS

CROSS-REFERENCE TO RELATED APPLICATIONS

The present application is a continuation of International Patent Application No. PCT/US2017/050521, filed Sep. 7, 2017, which claims priority to U.S. Provisional Application No. 62/384,896, filed Sep. 8, 2016, the disclosures of which are herein incorporated by reference in their entirety for all purposes.

BACKGROUND OF THE INVENTION

Myasthenia gravis (MG) is a chronic neuromuscular autoimmune disease that arises from an antibody-mediated attack on acetylcholine receptors (AChRs), resulting in the destruction of the postsynaptic membrane folded architecture and a decrease in AChR density in neuromuscular junctions. The loss of AChR results in generalized muscle weakness, often in the limbs. Other symptoms include ptosis (drooping eye lids) and diplopia (double vision). MG can become fatal when the muscles that control breathing are affected. MG is estimated to affect between 50 and 200 million people, with between 3 and 30 million new diagnoses being made each year.

Unfortunately, there is no cure for MG. While multiple treatments for MG are available, the available treatment options are associated with significant adverse side effects. Accordingly, there is a need for new treatments and preventative measures for MG. The present invention satisfies this need, and provides related advantages as well.

BRIEF SUMMARY OF THE INVENTION

In one aspect, the present invention provides an isolated peptide comprising the amino acid sequence SEHETRLVAX$_1$LFZ$_1$LKWNPX$_2$DYGGX$_3$KKIHZ$_2$LX$_4$YTGH (SEQ ID NO:31) and amino acid modifications relative to the amino acid sequence set forth in SEQ ID NO:1 at two or more positions selected from the group consisting of $X_1$, $X_2$, $X_3$, and $X_4$, wherein $X_1$, $X_2$, $X_3$, and $X_4$ are independently selected amino acids and $Z_1$ and $Z_2$ are linker sequences of independent lengths comprising independently selected amino acids.

In some embodiments, the amino acid modifications are at $X_1$ and $X_2$ relative to the amino acid sequence set forth in SEQ ID NO:1. In some instances, $X_1$ is N, $X_2$ is A, the length of $Z_1$ is 4, and the length of $Z_2$ is 2 (SEQ ID NO:2). In other embodiments, the amino acid modifications are at $X_1$ and $X_3$ relative to the amino acid sequence set forth in SEQ ID NO:1. In some instances, $X_1$ is N, $X_3$ is I, the length of $Z_1$ is 4, and the length of $Z_2$ is 2 (SEQ ID NO:3). In some other embodiments, the amino acid modifications are at $X_1$ and $X_4$ relative to the amino acid sequence set forth in SEQ ID NO:1. In some instances, $X_1$ is N, $X_4$ is D, the length of $Z_1$ is 4, and the length of $Z_2$ is 2 (SEQ ID NO:4). In some embodiments, the amino acid modifications are at $X_3$ and $X_4$ relative to the amino acid sequence set forth in SEQ ID NO:1. In some instances, the amino acid sequence is not SEQ ID NO:5.

In some other embodiments, the amino acid modifications are at $X_1$, $X_3$, and $X_4$ relative to the amino acid sequence set forth in SEQ ID NO:1. In some instances, $X_1$ is N, $X_3$ is I, $X_4$ is D, the length of $Z_1$ is 4, and the length of $Z_2$ is 2 (SEQ ID NO:6). In yet other embodiments, the amino acid modifications are at $X_1$, $X_2$, $X_3$, and $X_4$ relative to the amino acid sequence set forth in SEQ ID NO:1. In some instances, $X_1$ is N, $X_2$ is A, $X_3$ is I, $X_4$ is D, the length of $Z_1$ is 4, and the length of $Z_2$ is 2 (SEQ ID NO:7).

In other embodiments, the peptide binds to an antibody that binds to the main immunogenic region (MIR) of an acetylcholine receptor (AChR). In still other embodiments, the peptide further comprises an intein-chitin biding domain tag. In some embodiments, the peptide further comprises a hexahistidine tag. In some other embodiments, the peptide further comprises an antibody heavy chain fragment that is conjugated to the peptide. In some instances, the antibody is human immunoglobulin G. In other instances, the hinge region of the heavy chain fragment is conjugated to the C-terminal end of the peptide.

In another aspect, the present invention provides a composition comprising a peptide of the present invention or a plurality thereof.

In some embodiments, the composition further comprises a pharmaceutically acceptable carrier. In other embodiments, the plurality of peptides comprises at least 2, 3, 4, or 5 different peptides.

In yet another aspect, the present invention provides a kit comprising a peptide of the present invention or a plurality thereof and a solid support. In another aspect, the present invention provides an isolated nucleic acid encoding an isolated peptide of the present invention.

In some embodiments, the solid support is a multiwell plate, an ELISA plate, a microarray, a chip, a bead, a porous strip, or a nitrocellulose filter. In some instances, the bead comprises chitin. In other embodiments, the peptide or plurality thereof is immobilized on the solid support. In some other embodiments, the plurality of peptides binds to the same antibody or different antibodies that bind to the main immunogenic region (MIR) of an acetylcholine receptor (AChR). In still other embodiments, the kit further comprises instructions for use.

In another aspect, the invention provides methods for detecting or determining the severity of myasthenia gravis (MG) in a subject, the method comprising detecting in a biological sample from the subject the presence or absence of antibodies that bind to a peptide of the present invention or a plurality thereof, wherein the presence of antibodies that bind to the peptide or plurality thereof indicates the presence or an increased severity of MG.

In some embodiments, the antibodies bind to the main immunogenic region (MIR) of an acetylcholine receptor (AChR). In other embodiments, the peptide or plurality thereof is selected from the group consisting of SEQ ID NOS:2, 3, 4, 6, and 7.

In some other embodiments, the method further comprises obtaining the sample from the subject. In some instances, the sample is whole blood, serum, or plasma.

In particular embodiments, the peptide or plurality thereof is attached to a solid support. In some instances, the solid support is a multiwell plate, an ELISA plate, a microarray, a chip, a bead, a porous strip, or a nitrocellulose filter. In some instances, the bead comprises chitin. In some other embodiments, the antibodies are detected by Western blot, dot blot, ELISA, radioimmunoassay, immunoprecipitation, electrochemiluminescence, immunofluorescence, FACS analysis, or multiplex bead assay.

In other embodiments, the sample is compared to a control. In some instances, the control is obtained from a subject who does not have MG. In other instances, the control is obtained from the subject before developing symptoms of MG or after receiving treatment for MG.

In another aspect, the invention provides a method for preventing or treating myasthenia gravis (MG) in a subject, the method comprising administering to the subject a therapeutically effective amount of a peptide of the present invention or a plurality thereof, wherein the peptide or plurality thereof binds to antibodies circulating in the subject to form neutralizing complexes, thereby preventing or treating MG.

In some embodiments, the circulating antibodies bind to the main immunogenic region (MIR) of an acetylcholine receptor (AChR). In other embodiments, the peptide or plurality thereof is selected from the group consisting of SEQ ID NOS:2, 3, 4, 6, and 7. In still other embodiments, the peptide or plurality thereof inactivates or reduces the number of memory B-cells that produce antibodies that bind to the MIR of an AChR.

In other embodiments, the subject is exhibiting symptoms of MG. In some instances, treating the subject results in a decrease in the symptoms of MG. In still other embodiments, the method further comprises removing the neutralizing complexes from the subject. In some instances, the neutralizing complexes are removed by affinity plasmapheresis. In other embodiments, the peptide or plurality thereof is administered intravenously, intramuscularly, or a combination thereof.

Other objects, features, and advantages of the present invention will be apparent to one of skill in the art from the following detailed description and figures.

BRIEF DESCRIPTION OF THE DRAWINGS

FIG. 2 shows the sequences of the *Torpedo* 39MIR (SEQ ID NO:9), mouse 39MIR (SEQ ID NO:10), and human 39MIR (SEQ ID NO:8) peptides. Amino acid position numbers shown at the top correspond to those of the AChR alpha subunit amino acid sequence set forth in SEQ ID NO:28. The three non-contiguous alpha subunit segments (corresponding to amino acids 1-12, 65-79, and 110-115) are joined by linkers, denoted by underlined amino acids.

FIG. 4 shows the sequences of the *Torpedo* 39MIR (SEQ ID NO:9) and human 39MIR (SEQ ID NO:8) peptides, as well as the sequences of eight mutant *Torpedo* 39MIR peptides (N10K (SEQ ID NO:11), L12F (SEQ ID NO:12), R66K (SEQ ID NO:13), A70D (SEQ ID NO:14), I75V (SEQ ID NO:15), R79H (SEQ ID NO:16), D111Q (SEQ ID NO:17), and K115H (SEQ ID NO:18)). Amino acid position numbers shown at the top correspond to those of the AChR alpha subunit amino acid sequence set forth in SEQ ID NO:28. The three non-contiguous alpha subunit segments (corresponding to amino acids 1-12, 65-79, and 110-115) are joined by linkers, denoted by underlined amino acids.

FIG. 6 shows the sequences of the human 39MIR (SEQ ID NO:8) peptide and four mutant human 39MIR peptides (K10N (SEQ ID NO:19), D70A (SEQ ID NO:20), V75I (SEQ ID NO:21), and Q111D (SEQ ID NO:22)). Amino acid position numbers shown at the top correspond to those of the AChR alpha subunit amino acid sequence set forth in SEQ ID NO:28. The three non-contiguous alpha subunit segments (corresponding to amino acids 1-12, 65-79, and 110-115) are joined by linkers, denoted by underlined amino acids.

FIG. 8A shows a stereo view of the ECD of the alpha subunit from *Torpedo*. FIG. 8B shows a stereo view of the ECD of the alpha subunit from mouse.

FIG. 9A shows a stereo view of the ECD of the alpha subunit from *Torpedo*. FIG. 9B shows a stereo view of the ECD of the alpha subunit from mouse.

FIG. 10A shows a stereo view of the ECD of the alpha subunit from *Torpedo*. FIG. 10B shows a stereo view of the ECD of the alpha subunit from mouse.

FIG. 12A shows a peptide of the present invention (SEQ ID NO:27) and its relationship to the structure of the MIR of an AChR. FIG. 12B shows the peptide conjugated to an antibody Fc domain.

FIG. 14A shows that conjugates of the present invention can block the combining sites of pathogenic antibodies. FIG. 14B shows the various mechanisms by which the conjugates can inactivate and reduce the number of B-cells involved in making pathogenic mAbs.

DETAILED DESCRIPTION OF THE INVENTION

I. Introduction

Figure 1:
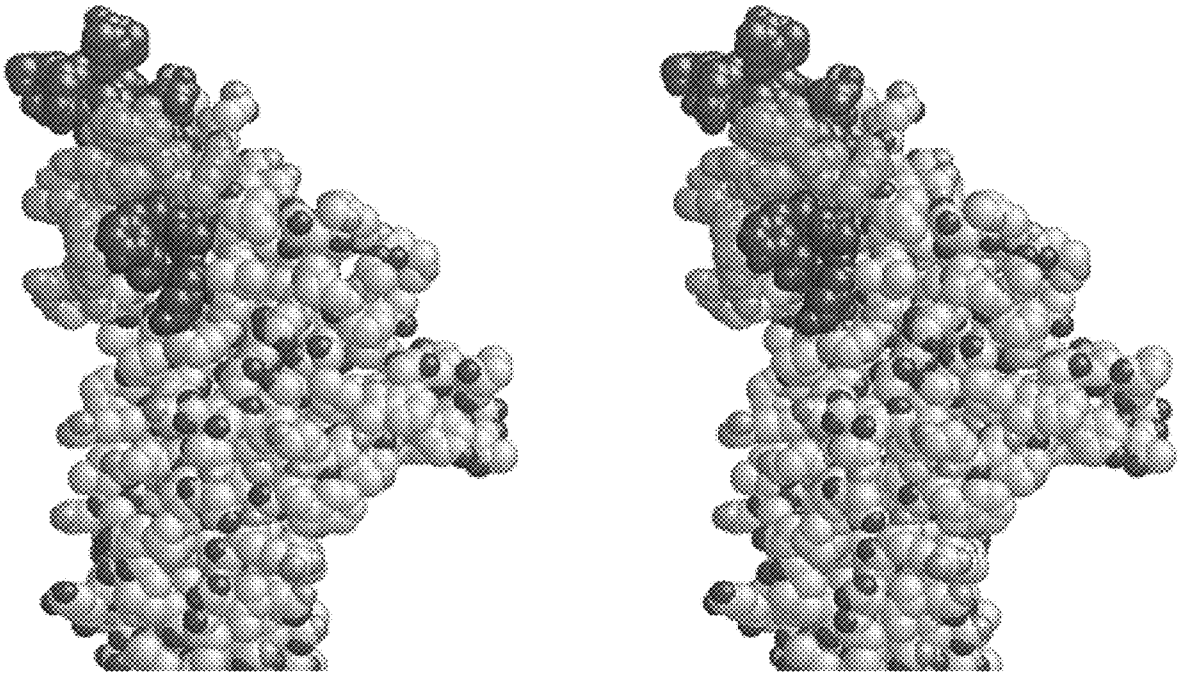
FIG. 1 shows a stereo view of the main immunogenic region (MIR) of the *Torpedo* acetylcholine receptor (AChR), depicting a Corey-Pauling-Koltun (CPK) space-filling model of the extracellular domain (ECD) of the alpha subunit. The MIR is located at the top of the ECD on the alpha subunit of the AChR.

Nicotinic acetylcholine receptors (AChRs) are expressed in high densities at the crests of the folds of postsynaptic membranes of neuromuscular junctions. The AChR is a 290 kDa integral membrane protein with an extracellular domain (ECD) that binds acetylcholine. Myasthenia gravis (MG) is an autoimmune disease that develops due to B-cell directed T-cell regulated production of pathogenic antibodies that are directed to protein components of neuromuscular junctions (NMJs). In most cases, the target of the antibodies is the AChR. The binding of anti-AChR antibodies to the AChR initiates the immune system destruction of the postsynaptic membrane folded architecture and concomitant loss of receptor density.

The present invention is based, in part, on the design of peptides that can bind to pathogenic antibodies that bind to the main immunogenic region (MIR) of an AChR. The peptides, conjugates comprising the peptides and antibody fragments, and methods of use thereof are useful for detecting or determining the severity of MG, as well as preventing and treating MG.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

Unless specifically indicated otherwise, the positions of amino acid modifications refer to positions within the amino acid sequence of the nicotinic AChR alpha subunit. As an example, the sequence for *Torpedo californica* nicotinic AChR alpha subunit amino acids 1-161 of the extracellular domain is provided in SEQ ID NO:28. As a non-limiting example, a "Q111" modification means that the amino acid corresponding to the $111^{th}$ amino acid in a nicotinic AChR alpha subunit, which is normally Q in the reference sequence (e.g., human sequence) has been modified. The modification can comprise a substitution to any amino acid other than Q, an insertion, or a deletion. Similarly, a "Q111D" modification means that the amino acid corresponding to the $111^{th}$ amino acid in a nicotinic AChR alpha subunit, which is normally Q in the reference sequence (e.g., human sequence) has been substituted with the amino acid D.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "subject," "individual," and "patient" are used interchangeably herein to refer to a vertebrate, preferably a mammal, more preferably a human. Mammals include, but are not limited to, murines, rats, simians, humans, farm animals, sport animals, and pets. Tissues, cells and their progeny of a biological entity obtained in vivo or cultured in vitro are also encompassed.

The term "severity" when used in the context of disease severity (e.g., the severity of myasthenia gravis), can refer to, as a non-limiting example, one or more signs or symptoms that are observable on physical exam. For example, severity can refer to a qualitative or quantitative measurement of muscle weakness. Severity can also refer to how many muscles or body systems are exhibiting muscle weakness. Furthermore, severity can also refer to other sequelae resulting from the disease. For example, the development of shortness of breath can be construed as an increase in severity compared to before shortness of breath developed. As another non-limiting example, severity can reflect one or more measurable values. For example, blood oxygen levels, heart rate, blood pressure, the results of laboratory tests (e.g., the presence of antibodies or other biomarkers in a sample), radiographic or other imaging results, and electromyelogram readings can all be used as indicators of disease severity. As yet another non-limiting example, severity may be determined by, or be related to, how quickly signs, symptoms, or other observable or measurable phenomena change, and/or whether the changes are permanent or transient. Methods and criteria for determining disease severity will be known to one of skill in the art.

As used herein, the term "administering" includes oral administration, topical contact, administration as a suppository, intravenous, intraperitoneal, intramuscular, intralesional, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "treating" refers to an approach for obtaining beneficial or desired results including, but not limited to, a therapeutic benefit and/or a prophylactic benefit. By therapeutic benefit is meant any therapeutically relevant improvement in or effect on one or more diseases, conditions, or symptoms under treatment. Therapeutic benefit can also mean to effect a cure of one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "sufficient amount" refers to the amount of a peptide, nucleic acid, or composition that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

For the purposes herein an effective amount is determined by such considerations as may be known in the art. The amount must be effective to achieve the desired therapeutic effect in a subject suffering from myasthenia gravis. The desired therapeutic effect may include, for example, amelioration of undesired symptoms associated with myasthenia gravis, prevention of the manifestation of such symptoms before they occur, slowing down the progression of symptoms associated with myasthenia gravis, slowing down the deterioration of muscle function associated with myasthenia gravis, slowing down or limiting any irreversible damage caused by myasthenia gravis, lessening the severity of or curing myasthenia gravis, or improving the survival rate or providing more rapid recovery from myasthenia gravis. Further, in the context of prophylactic treatment the amount may also be effective to prevent the development of myasthenia gravis.

The effective amount depends, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the molecule (e.g., peptide) for its target, its distribution profile within the body, the relationship between a variety of pharmacological parameters (e.g., half-life in the body) and undesired side effects, and other factors such as age and gender, etc.

The term "pharmaceutically acceptable carrier" refers to a substance that aids the administration of an active agent to a cell, an organism, or a subject. "Pharmaceutically acceptable carrier" refers to a carrier or excipient that can be included in the compositions of the invention and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc. In some instances, the carrier is an agent that facilitates the delivery of a peptide to a target cell or tissue. One of skill in the art will recognize that other pharmaceutical carriers are useful in the present invention.

The term "myasthenia gravis (MG)" refers to an autoimmune disease that causes progressive muscle weakness in multiple regions of the body and results, at least in part, from a B-cell directed T-cell regulated production of pathogenic antibodies that are directed to protein components of neuromuscular junctions. In particular, many of the antibodies bind to nicotinic acetylcholine receptors (AChRs) in neuromuscular junctions, resulting in the destruction of the postsynaptic membrane folded architecture and concomitant loss of AChR density. The destruction of postsynaptic membrane architecture and reduction of AChR density leads to a decreased or complete loss of the ability for muscles to respond to neurotransmitter signals.

Early symptoms of MG commonly result from weakness in the extraocular muscles. Common early symptoms include diplopia (i.e., double vision) and ptosis (i.e., difficulty in raising the eyelids). Common early symptoms also include difficulty chewing, swallowing, and choking, due to the development of weakness in the bulbar muscles. Weakness can subsequently progress to other facial muscles, neck, arms, legs, and torso, causing symptoms such as difficulty lifting objects, walking, holding one's head up, and speaking. Eventually, muscle weakness can progress to the point where the patient has difficulty breathing, and in some instances will develop respiratory In some cases MG will result in death.

Diagnosing MG can include obtaining a detailed medical history, performing a careful physical exam, obtaining an electromyelogram to assess the response of specific muscles to electrical stimulation, laboratory tests (e.g., blood tests), and CT imaging.

The term "*Torpedo*" refers to a genus of rays, also commonly called "electric rays," "torpedo rays," or "torpedoes". AChRs have been extensively studied, for example, in *Torpedo californica*. Other species of *Torpedo* include but are not limited to *Torpedo adenensis, Torpedo alexandrinsis, Torpedo andersoni, Torpedo bauchotae, Torpedo fuscomaculata, Torpedo mackayana, Torpedo marmorata, Torpedo microdiscus, Torpedo panthera, Torpedo semipelagica, Torpedo sinuspersici, Torpedo suessii*, and *Torpedo* torpedo.

The term "acetylcholine receptor (AChR)" refers an integral membrane protein that responds to the binding of the neurotransmitter acetylcholine. AChRs are broadly grouped into two groups: muscarinic and nicotinic AChRs. Muscarinic AChRs are G-protein coupled receptors that activate ion channels via second messenger signaling. Muscarinic AChRs function as the main end-receptor stimulated by acetylcholine that is released from postganglionic fibers of the parasympathetic nervous system. Muscarinic AChRs also function in the recovery of postganglionic neurons (hyperpolarization and slow depolarization, as opposed to fast depolarization which is facilitated by nicotinic AChRs), and are found in innervated tissue (e.g., muscarinic AChRs are found in sweat glands) and are distributed in both pre-synaptic and post-synaptic locations throughout the central nervous system. Muscarinic AChRs comprise five types ($M_1$, $M_2$, $M_3$, $M_4$, and $M_5$), although other classification systems are used, depending on the particular context.

Nicotinic AChRs are Cys-loop proteins that are ligand-gated ion channels which respond to drugs, including nicotine, in addition to responding to acetylcholine. Nicotinic AChRs play at least two important roles in the peripheral nervous system. The first role is that nicotinic AChRs pass signals from presynaptic cells to postsynaptic cells of the sympathetic and parasympathetic nervous systems. The second significant peripheral nervous system role is that nicotinic AChRs are found on skeletal muscle and receive signals required for muscle contractions. Nicotinic AChRs are non-selectively permeable to cations, allowing sodium, potassium, and calcium to pass through an open channel, depending on the particular combination of subunits in a given channel. Typically, upon channel opening sodium will pass into a cell and potassium will leave the cell, with a net inward flux of these cations. The passage of calcium through nicotinic AChRs can lead to the release of other neurotransmitters and the activation of other processes via second messenger signaling (e.g., gene regulatory processes).

Figure 12A:
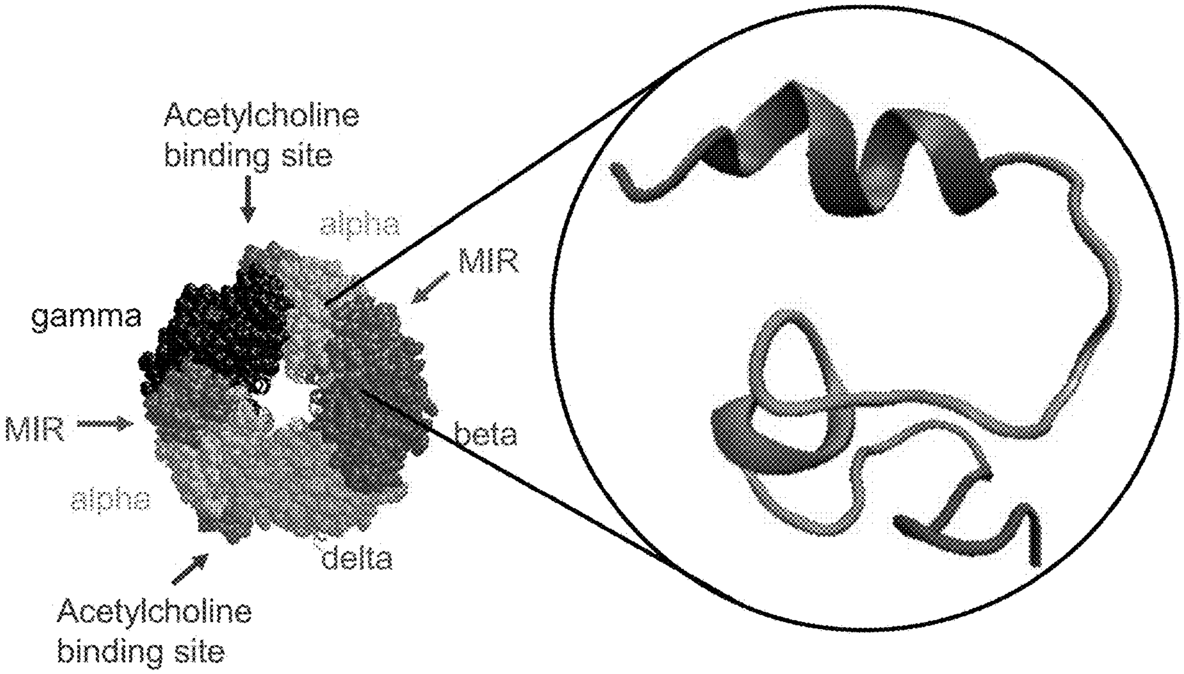
FIGS. 12A and 12B show compositions of the present invention.

Nicotinic AChRs have a molecular mass of about 290 kDa and comprise five subunits that are arranged symmetrically around a central pore (e.g., see the *Torpedo* example illustrated in FIG. 12A). In vertebrates, nicotinic AChRs are classified as either muscle-type or neuronal-type receptors. Neuronal type receptors can comprise various homomeric and heteromeric combinations of twelve different subunits: α2, α3, α4, α5, α6, α7, α8, α9, α10, β2 β3, and β4. For muscle-type receptors, which are found in neuromuscular junctions, the embryonic form of the receptor comprises α, β, γ, and δ subunits, which are present in a 2:1:1:1 ratio, while the adult form comprises α1, β1, δ, and ε subunits, which are present in a 2:1:1:1 ratio.

The term "main immunogenic region (MIR)" refers to a region of the extracellular domain of the nicotinic AChR alpha subunit that commonly serves as the binding site for antibodies that target the nicotinic AChR. The MIR typically comprises three non-contiguous segments of the alpha subunit that are arranged in close physical proximity following protein folding. As one non-limiting example, the MIR can comprise amino acids 1-12, 65-79, and 110-115 of the nicotinic AChR alpha subunit.

The terms "polypeptide," "peptide," and "protein" are used interchangeably herein to refer to a polymer of amino acid residues, or an assembly of multiple polymers of amino acid residues. The terms apply to amino acid polymers in which one or more amino acid residue is an artificial chemical mimic of a corresponding naturally occurring amino acid, as well as to naturally occurring amino acid polymers and non-naturally occurring amino acid polymer.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an a carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins,* 1993).

The term "amino acid modification" refers to a substitution, a deletion, or an insertion of one or more amino acids.

The term "nucleic acid," "nucleotide" or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

The term "nucleotide sequence encoding a peptide" or "gene" means the segment of DNA involved in producing a peptide chain, it includes regions preceding and following the coding region (leader and trailer) involved in the transcription/translation of the gene product and the regulation of the transcription/translation, as well as intervening sequences (introns) between individual coding segments (exons).

The term "neutralizing complex" refers to a complex comprising an antibody bound to a peptide that prevents/inhibits/blocks the antibody from binding to its antigen (e.g., the MIR of an AChR).

The term "affinity plasmapheresis" refers to an extracorporeal blood purification procedure for the removal of deleterious agents (e.g., disease-causing agents) from the plasma of a subject.

"Percentage of sequence identity" is determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

The term "percent identity" or "percent sequence identity," in the context of describing two or more polynucleotide or amino acid sequences, refers to two or more sequences or subsequences that are the same or have a specified percentage of amino acid residues or nucleotides that are the same (for example, a variant of a peptide of interest). When a peptide or polynucleotide has at least about 80% sequence identity, preferably at least about 85%, 86%, 87%, 88%, 89%, 90%, 91%, 92%, 93, 94%, 95%, 96%, 97%, 98%, 99%, or 100% identity, to a reference sequence, when compared and aligned for maximum correspondence over a comparison window, or designated region as measured using one of the following sequence comparison algorithms or by manual alignment and visual inspection, such sequences are then said to be "substantially identical." With regard to polynucleotide sequences, this definition also refers to the complement of a test sequence. Preferably, the identity exists over a region that is at least about 6, 7, or 8 amino acids in length, or more preferably over a region that is at least 6-25 or at least 6-12 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

Methods of alignment of sequences for comparison are well-known in the art.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Additional examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA,* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or peptides are substantially identical is that the peptide encoded by the first nucleic acid is immunologically cross reactive with the antibodies raised against the peptide encoded by the second nucleic acid. Thus, a peptide is typically substantially identical to a second peptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

III. Detailed Description of the Embodiments

A. Isolated Peptides

In one aspect, the present invention provides an isolated peptide comprising the amino acid sequence SEHETRLVA$X_1$LF$Z_1$LKWNP$X_2$DYGG$X_3$KKIH$Z_2$L$X_4$YTGH (SEQ ID NO:31). In some embodiments, the peptide further comprises amino acid modifications relative to the amino acid sequence set forth in SEQ ID NO:1 at two or more positions selected from the group consisting of $X_1$, $X_2$, $X_3$, and $X_4$, wherein $X_1$, $X_2$, $X_3$, and $X_4$ are independently selected amino acids and $Z_1$ and $Z_2$ are linker sequences of independent lengths comprising independently selected amino acids. For example, amino acid modifications can be made with respect to the amino acid sequence set forth in SEQ ID NO:1 at $X_1$ and $X_2$, $X_1$ and $X_3$, $X_1$ and $X_4$, $X_2$ and $X_3$, $X_2$ and $X_4$, $X_3$ and $X_4$, $X_1$, $X_2$, and $X_3$, $X_1$, $X_2$, and $X_4$, $X_1$, $X_3$, and $X_4$, $X_2$, $X_3$, and $X_4$, or $X_1$, $X_2$, $X_3$, and $X_4$.

The linkers $Z_1$ and $Z_2$ comprise independently selected amino acids. The amino acids can be any amino acid. In preferred embodiments, $Z_1$ and $Z_2$ comprise the amino acids G and S. In some instances $Z_1$ comprises the amino acid sequence GGGS. In other instances, $Z_2$ comprises the amino acid sequence GS. In some instances, $Z_1$ and $Z_2$ are of the same length. In other instances, $Z_1$ and $Z_2$ are of different lengths. The length of each linker can be any length. In some embodiments the linkers are between about 1 and 10 (i.e., about 1, 2, 3, 4, 5, 6, 7, 8, 9, or 10) amino acids long. In other embodiments, the linkers are between about 10 and 30 (i.e., about 10, 11, 12, 13, 14, 15, 16, 17, 18, 19, 20, 21, 22, 23, 24, 25, 26, 27, 28, 29, or 30) amino acids long. In still other embodiments, the linkers are between about 30 and 100 (i.e., about 30, 35, 40, 45, 50, 55, 60, 65, 70, 75, 80, 85, 90, or 100) amino acids long.

In some embodiments, the peptide comprises amino acid modifications at two or more positions selected from the group consisting of K10, D22, V27, and Q35 relative to the amino acid sequence set forth in SEQ ID NO:8, where K10, D22, V27, and Q35 denote positions within the peptide.

In some embodiments, the amino acid modifications are at $X_1$ and $X_2$ relative to the amino acid sequence set forth in SEQ ID NO:1. In some instances, $X_1$ is N, $X_2$ is A, the length of $Z_1$ is 4, and the length of $Z_2$ is 2 (SEQ ID NO:2). In other embodiments, the amino acid modifications are at positions K10 and D22 relative to the amino acid sequence set forth in SEQ ID NO:8, where K10 and D22 denote positions within the peptide. In some instances, the peptide comprises the amino acid sequence set forth in SEQ ID NO:23.

In some embodiments, the amino acid modifications are at $X_1$ and $X_3$ relative to the amino acid sequence set forth in SEQ ID NO:1. In some instances, $X_1$ is N, $X_3$ is I, the length of $Z_1$ is 4, and the length of $Z_2$ is 2 (SEQ ID NO:3). In other embodiments, the amino acid modifications are at positions K10 and V27 relative to the amino acid sequence set forth in SEQ ID NO:8, where K10 and V27 denote positions within the peptide. In some instances, the peptide comprises the amino acid sequence set forth in SEQ ID NO:24.

In some embodiments, the amino acid modifications are at $X_1$ and $X_4$ relative to the amino acid sequence set forth in SEQ ID NO:1. In some instances, $X_1$ is N, $X_4$ is D, the length of $Z_1$ is 4, and the length of $Z_2$ is 2 (SEQ ID NO:4). In other embodiments, the amino acid modifications are at positions K10 and Q35 relative to the amino acid sequence set forth in SEQ ID NO:8, where K10 and Q35 denote positions within the peptide. In some instances, the peptide comprises the amino acid sequence set forth in SEQ ID NO:25.

In some embodiments, the amino acid modifications are at $X_3$ and $X_4$ relative to the amino acid sequence set forth in SEQ ID NO:1. In other embodiments, the amino acid modifications are at positions V27 and Q35 relative to the amino acid sequence set forth in SEQ ID NO:8, where V27 and Q35 denote positions within the peptide. In some instances, the amino acid sequence of the peptide is not SEQ ID NO:5.

In some embodiments, the amino acid modifications are at $X_1$, $X_3$, and $X_4$ relative to the amino acid sequence set forth in SEQ ID NO:1. In some instances, $X_1$ is N, $X_3$ is I, $X_4$ is D, the length of $Z_1$ is 4, and the length of $Z_2$ is 2 (SEQ ID NO:6). In other embodiments, the amino acid modifications are at positions K10, V27, and Q35 relative to the amino acid sequence set forth in SEQ ID NO:8, where K10, V27, and Q35 denote positions within the peptide. In some instances, the peptide comprises the amino acid sequence set forth in SEQ ID NO:26.

In some embodiments, the amino acid modifications are at $X_1$, $X_2$, $X_3$, and $X_4$ relative to the amino acid sequence set forth in SEQ ID NO:1. In some instances, $X_1$ is N, $X_2$ is A, $X_3$ is I, $X_4$ is D, the length of $Z_1$ is 4, and the length of $Z_2$ is 2 (SEQ ID NO:7). In other embodiments, the amino acid modifications are at positions K10, D22, V27, and Q35 relative to the amino acid sequence set forth in SEQ ID NO:8, where K10, D22, V27, and Q35 denote positions within the peptide. In some instances, the peptide comprises the amino acid sequence set forth in SEQ ID NO:27. In particular instances, the peptide does not consist of the amino acid sequence set forth in SEQ ID NO:29.

In some embodiments, the peptide has at least about 80% sequence identity (e.g., at least about 80%, 81%, 82%, 83%, 84%, 85%, 86%, 87%, 88%, 89%, 90%, 91%, 92%, 93%, 94%, 95%, 96%, 97%, 98%, or 99% sequence identity) to any one of the amino acid sequences set forth in SEQ ID NOS:1, 2, 3, 4, 6, and 7. In some embodiments, the peptide has at least about 90% sequence identity (e.g., at least about 90%, 91%, 92%, 93%, 94%, 95%, 96%, 97%, 98%, or 99% sequence identity) to any one of the amino acid sequences set forth in SEQ ID NOS:1, 2, 3, 4, 6, and 7. In some embodiments, the peptide has at least about 95% sequence identity (e.g., at least about 95%, 96%, 97%, 98%, or 99% sequence identity) to any one of the amino acid sequences set forth in SEQ ID NOS:1, 2, 3, 4, 6, and 7. In particular embodiments, linker sequences (e.g., $Z_1$ and/or $Z_2$ linker sequences) are not taken into account when determining the percent sequence identity.

In some embodiments, the peptide comprises an amino acid sequence comprising or consisting of any one of the amino acid sequences set forth in SEQ ID NOS:1, 2, 3, 4, 6, and 7. In some embodiments, the peptide (e.g., isolated peptide) has 100% sequence identity to any one of the amino acid sequences set forth in SEQ ID NOS:1, 2, 3, 4, 6, and 7. In some embodiments, the peptide (e.g., isolated peptide) comprises and amino acid sequence consisting of any one of the amino acid sequences set forth in SEQ ID NOS:1, 2, 3, 4, 6, and 7. In particular embodiments, linker sequences (e.g., $Z_1$ and/or $Z_2$ linker sequences) are not taken into account when determining the percent sequence identity.

In some embodiments, the peptide has at least about 80% sequence identity (e.g., at least about 80%, 81%, 82%, 83%, 84%, 85%, 86%, 87%, 88%, 89%, 90%, 91%, 92%, 93%, 94%, 95%, 96%, 97%, 98%, or 99% sequence identity) to any one of the amino acid sequences set forth in SEQ ID NOS:23, 24, 25, 26, 27, and 30. In some embodiments, the peptide has at least about 90% sequence identity (e.g., at least about 90%, 91%, 92%, 93%, 94%, 95%, 96%, 97%, 98%, or 99% sequence identity) to any one of the amino acid sequences set forth in SEQ ID NOS:23, 24, 25, 26, 27, and 30. In some embodiments, the peptide has at least about 95% sequence identity (e.g., at least about 95%, 96%, 97%, 98%, or 99% sequence identity) to any one of the amino acid sequences set forth in SEQ ID NOS:23, 24, 25, 26, 27, and 30. In particular embodiments, linker sequences (e.g., $Z_1$ linker sequences such as GGGS and/or $Z_2$ linker sequences such as GS) are not taken into account when determining the percent sequence identity.

In some embodiments, the peptide comprises an amino acid sequence comprising or consisting of any one of the amino acid sequences set forth in SEQ ID NOS:23, 24, 25, 26, 27, and 30. In some embodiments, the peptide (e.g., isolated peptide) has 100% sequence identity to any one of the amino acid sequences set forth in SEQ ID NOS:23, 24, 25, 26, 27, and 30. In some embodiments, the peptide (e.g., isolated peptide) comprises and amino acid sequence consisting of any one of the amino acid sequences set forth in SEQ ID NOS:23, 24, 25, 26, 27, and 30. In particular embodiments, linker sequences (e.g., $Z_1$ linker sequences such as GGGS and/or $Z_2$ linker sequences such as GS) are not taken into account when determining the percent sequence identity.

In some embodiments, the peptide comprises at least about 6, 7, 8, 9, 10, 11, 12, 13, 14, or 15 contiguous amino acids of any one of the amino acid sequence set forth in SEQ ID NOS:1, 2, 3, 4, 6, 7, 23, 24, 25, 26, 27, and 30. In some embodiments, the peptide comprises an amino acid sequence comprising or consisting of at least about 6, 7, 8, 9, 10, 11, 12, 13, 14, or 15 contiguous amino acids as set forth in any one of SEQ ID NOS:1, 2, 3, 4, 6, 7, 23, 24, 25, 26, 27, and 30.

In some embodiments, the peptide is between about 6 and about 50 (e.g., about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) amino acids in length. In some embodiments, the peptide is between about 30 and about 40 (e.g., about 30, 31, 32, 33, 34, 35, 36, 37, 38, 39, or 40) amino acids in length. In particular embodiments, the peptide is about 39 amino acids in length. In some embodiments, the peptide is at least about 50 amino acids (e.g., at least about 50, 55, 60, 65, 70, 75, 80, 85, 90, 95, 100, or more) amino acids in length.

In some embodiments, the peptide binds to an antibody that binds to the main immunogenic region (MIR) of an acetylcholine receptor (AChR). In some instances, the AChR is a nicotinic AChR. In still other embodiments, the peptide further comprises an intein-chitin biding domain tag. In some embodiments, the peptide further comprises a polyhistidine tag. In some instances, the polyhistidine tag is a hexahistidine tag.

In some embodiments, the peptide further comprises one or more antibodies or antibody fragments that are conjugated to the peptide. The antibodies or fragments thereof can comprise one or more light chains, heavy chains, fragments thereof, or combinations thereof. Any fragment or combination of heavy chain domains or regions can be conjugated to the peptide, including the variable domain ($V_H$), hinge region, and constant ($C_H1$, $C_H2$, and $C_H3$) domains. In particular instances, the hinge region of the antibody fragment is conjugated to the C-terminal end of the peptide. In other instances, the antibody fragment comprises the hinge region, $C_H2$ domain, and $C_H3$ domain of the heavy chain. In particular instances, the antibody fragment comprises the hinge region and $C_H2$ and $C_H3$ domains of a human IgG heavy chain. In some instances, the one or antibody fragments comprise one or more Fc domains, one or more Fab domains, or a combination thereof.

Antibodies or fragments thereof from any number of animals can be conjugated to peptides of the present invention (e.g., rabbits, goats, birds, mice, rats, reptiles, sharks, primates, humans). In preferred embodiments, the one or more antibodies or fragments thereof are human. In some instances, the antibodies or fragments thereof are from human IgA, IgD, IgE, IgG, IgM, or a combination thereof. In particular instances, the antibody or fragment thereof is from human IgG.

B. Isolated Nucleic Acids

In another aspect, the present invention provides an isolated nucleic acid that encodes an isolated peptide described herein. In some embodiments, the nucleic acid encodes a peptide that has at least about 80% sequence identity (e.g., at least about 80%, 81%, 82%, 83%, 84%, 85%, 86%, 87%, 88%, 89%, 90%, 91%, 92%, 93%, 94%, 95%, 96%, 97%, 98%, or 99% sequence identity) to any one of the amino acid sequences set forth in SEQ ID NOS:1, 2, 3, 4, 6, 7, 23, 24, 25, 26, 27, and 30. In some embodiments, the nucleic acid encodes a peptide that has at least about 90% sequence identity (e.g., at least about 90%, 91%, 92%, 93%, 94%, 95%, 96%, 97%, 98%, or 99% sequence identity) to any one of the amino acid sequences set forth in SEQ ID NOS:1, 2, 3, 4, 6, 7, 23, 24, 25, 26, 27, and 30. In some embodiments, the nucleic acid encodes a peptide that has at least about 95% sequence identity (e.g., at least about 95%, 96%, 97%, 98%, or 99% sequence identity) to any one of the amino acid sequences set forth in SEQ ID NOS:23, 24, 25, 26, 27, and 30. In particular embodiments, linker sequences (e.g., $Z_1$ linker sequences such as GGGS and/or $Z_2$ linker sequences such as GS) are not taken into account when determining the percent sequence identity. In some instances, the amino acid sequence of the peptide encoded by the nucleic acid is not SEQ ID NO:5. In other instances, the amino acid sequence of the peptide encoded by the nucleic acid is not SEQ ID NO:29.

In some embodiments, the nucleic acid encodes a peptide that comprises at least about 6, 7, 8, 9, 10, 11, 12, 13, 14, or 15 contiguous amino acids of any one of the amino acid sequence set forth in SEQ ID NOS:1, 2, 3, 4, 6, 7, 23, 24, 25, 26, 27, and 30. In some embodiments, the nucleic acid encodes a peptide that comprises an amino acid sequence comprising or consisting of at least about 6, 7, 8, 9, 10, 11, 12, 13, 14, or 15 contiguous amino acids as set forth in any one of SEQ ID NOS:1, 2, 3, 4, 6, 7, 23, 24, 25, 26, 27, and 30.

The present invention also provides a vector comprising an isolated nucleic acid provided herein, a host cell comprising a vector provided herein, and a peptide encoded by a nucleic acid provided herein. The vectors can include the peptide-encoding nucleic acid operably linked to suitable transcriptional and/or translational regulatory elements (e.g., a sequence to control expression) to effect expression in a suitable host cell. The regulatory elements may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful expression vectors can be constructed by methods known to one of ordinary skill in the art, and are also commercially available. Exemplary recombinant viral vectors include retrovirus, parvovirus, densovirus and baculovirus vectors.

The vector can include a strong constitutive or inducible promoter operatively linked to a nucleic acid provided herein. Suitable promoters are well known and readily available to one of ordinary skill in the art and include, for example, bacterial, yeast, viral, mammalian, and insect promoters. Exemplary expression vectors are vectors compatible with mammalian cells.

The host cell can include a vector or an isolated nucleic acid as provided herein. The host cell may be prokaryotic or eukaryotic, including bacterial, yeast, insect or mammalian cells. In some cases, the host cell can be a plant cell. In some embodiments, the host cells are plant, insect or mammalian cells. The isolated nucleic acids or vectors, e.g., expression vectors, may be introduced into the host cells by methods known to one of ordinary skill in the art, including transformation, transfection and infection. For example, transfection may be accomplished by any known method, such as liposome-mediated transfection, calcium phosphate-mediated transfection, naked DNA transfection, microinjection or electroporation. Transformation methods suitable for prokaryotic cells are described, for example, in Cohen et al., Proc. Natl. Acad. Sci. (USA) 69:2110 (1972). Transformation of eukaryotic host cells is described, for example, in Sambrook et al., Molecular Cloning: A Laboratory Manual, 3rd edition, Cold Spring Harbor Press, Cold Spring Harbor, N.Y. (2000). The host cells containing the isolated nucleic acid or vectors are useful for replicating the vector and expressing the nucleic acid encoding the peptide of interest, or for replicating and expressing the isolated nucleic acid.

C. Compositions

In another aspect, the invention provides compositions comprising a peptide of the present invention or a plurality thereof. In some embodiments, the compositions include any one of the isolated peptides described herein. In other embodiments, the compositions include two or more of any of the peptides provided herein. For example, the compositions may include 1, 2, 3, 4, 5, 6, 7, 8, 9, 10, or more different peptides. As a non-limiting example, the compositions may include peptides comprising amino acid sequences set forth in SEQ ID NOS:2, 3, 4, 6, 7, 23, 24, 25, 26, 27, or a combination thereof. In some embodiments, the composition includes one or more nucleic acids encoding peptides of the present invention.

In other embodiments, compositions of the present invention further comprise a pharmaceutically acceptable carrier. The formulation of pharmaceutical compositions is generally known in the art (see, e.g., *REMINGTON'S PHARMACEUTICAL SCIENCES,* $18^{TH}$ ED., Mack Publishing Co., Easton, Pa. (1990)). Prevention against microorganism contamination can be achieved through the addition of one or more of various antibacterial and antifungal agents.

Pharmaceutical forms suitable for administration include sterile aqueous solutions or dispersions and sterile powders for the extemporaneous preparation of sterile injectable solutions or dispersions. Typical carriers include a solvent or dispersion medium containing, for example, water-buffered aqueous solutions (i.e., biocompatible buffers), ethanol, polyols such as glycerol, propylene glycol, polyethylene glycol, suitable mixtures thereof, surfactants, or vegetable oils.

Sterilization can be accomplished by an art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing peptide(s) and/or composition(s) of the present invention is accomplished by incorporating the compound(s) in the required amount(s) in the appropriate solvent with various ingredients enumerated above, as required, followed by sterilization (e.g., filter sterilization). To obtain a sterile powder, the above sterile solutions are vacuum-dried or freeze-dried as necessary.

In some embodiments, the peptide(s) and/or composition(s) provided herein are formulated for administration, e.g., oral, nasal, topical, or parental administration in unit dosage form for ease of administration and uniformity of dosage. Unit dosage forms, as used herein, refers to physically discrete units suited as unitary dosages for the subjects, e.g., humans or other mammals to be treated, each unit containing a predetermined quantity of active material calculated to produce the desired therapeutic effect in association with the required pharmaceutical carrier. In some instances, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the peptide(s) and/or composition(s).

Methods for preparing such dosage forms are known to those skilled in the art (see, e.g., *REMINGTON'S PHARMACEUTICAL SCIENCES*, supra). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *REMINGTON'S PHARMACEUTICAL SCIENCES*, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

In some embodiments, the composition for administration may be an oral delivery vehicle such as a capsule, cachet or tablet, each of which contains a predetermined amount of the peptide to provide the correct incremental dose to the patient. Oral delivery vehicles may be useful, for example, in avoiding contact between the peptide and the mouth and upper gastrointestinal tract. For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with a peptide(s) and/or composition(s) described herein, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

In some embodiments, a suitable carrier masks the composition, e.g., the peptide, from the mouth and upper gastrointestinal (GI) tract and reduces or prevents local itching/swelling reactions in these regions during administration. For example, a carrier may contain one or more lipid, polysaccharide or protein constituents. In some cases, the carrier is a food product.

For topical administration, the therapeutically effective dose can be in the form of emulsions, lotions, gels, foams, creams, jellies, solutions, suspensions, ointments, and transdermal patches. For administration by inhalation, a peptide(s) and/or composition(s) described herein can be delivered as a dry powder or in liquid form via a nebulizer. Aerosol formulations can be placed into pressurized acceptable propellants such as dichlorodifluoromethane. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In some embodiments, the therapeutically effective dose may further comprise other components, for example, anti-allergy drugs, such as antihistamines, steroids, bronchodilators, leukotriene stabilizers and mast cell stabilizers. Suitable anti-allergy drugs are well known in the art.

D. Kits

In another aspect, the present invention provides kits comprising a peptide of the present invention or a plurality thereof and a solid support. The kits are useful for detecting or determining the severity of myasthenia gravis in a subject. The kits are also useful for preventing or treating myasthenia gravis in a subject.

Materials and reagents to carry out these various methods can be provided in kits to facilitate execution of the methods. As used herein, the term "kit" includes a combination of articles that facilitates a process, assay, analysis, or manipulation. In particular, kits comprising the peptides or compositions of the present invention find utility in a wide range of applications including, for example, diagnostics, prognostics, therapy, and the like.

In some embodiments, the kits comprise peptides that comprise the amino acid sequences set forth in SEQ ID NOS:2, 3, 4, 6, 7, 23, 24, 25, 26, 27, and combinations thereof. In other embodiments, the kits comprise at least one peptide (e.g., at least 1, 2, 3, 4, 5, 6, 7, 8, 9, 10, or more peptides). In some other embodiments, the one or plurality of peptides in the kits further comprise an antibody or fragment thereof that is conjugated to the peptide or plurality thereof.

In other embodiments, the plurality of peptides in the kits bind to the same anti-MIR antibody (i.e., an antibody that binds to the MIR of an AChR). In particular embodiments, the plurality of peptides bind to different anti-MIR antibodies.

In some embodiments, the solid support is a multiwell plate, an ELISA plate, a microarray, a chip, a bead, a porous strip, or a nitrocellulose filter. In some instances, the bead comprises chitin. In other embodiments, the peptide or plurality of peptides can be immobilized on the solid support. The immobilization can be via covalent or non-covalent binding. In some embodiments, the immobilization is through a capture antibody that specifically binds to the one or more peptides. In certain instances, the solid support in the kits are provided prepared with one or more immobilized peptides.

Kits can contain chemical reagents as well as other components. In addition, the kits of the present invention can include, without limitation, instructions to the kit user, apparatus and reagents for sample collection and/or purification, apparatus and reagents for product collection and/or purification, sample tubes, holders, trays, racks, dishes, plates, solutions, buffers or other chemical reagents, suitable samples to be used for standardization, normalization, and/or control samples. Kits of the present invention can also be packaged for convenient storage and safe shipping, for example, in a box having a lid.

In some embodiments, the kits also comprise labeled secondary antibodies used to detect the presence of anti-MIR autoantibodies that bind to one or more peptides. The secondary antibodies bind to the constant or "C" regions of different classes or isotypes of immunoglobulins IgM, IgD, IgG, IgA, and IgE. Usually, a secondary antibody against an IgG constant region is included in the kits, such as, e.g., secondary antibodies against one of the IgG subclasses (e.g., IgG1, IgG2, IgG3, and IgG4). Secondary antibodies can be labeled with any directly or indirectly detectable moiety, including a fluorophore (e.g., fluorescein, phycoerythrin, quantum dot, Luminex bead, fluorescent bead), an enzyme (e.g., peroxidase, alkaline phosphatase), a radioisotope (e.g., $^{3}H$, $^{32}P$, $^{125}I$) or a chemiluminescent moiety. Labeling signals can be amplified using a complex of biotin and a biotin binding moiety (e.g., avidin, streptavidin, neutravidin). Fluorescently labeled anti-human IgG antibodies are commercially available from Molecular Probes, Eugene, Oreg. Enzyme-labeled anti-human IgG antibodies are commercially available from Sigma-Aldrich, St. Louis, Mo. and Chemicon, Temecula, Calif.

The kits may further comprise instructions for contacting the solid support with a biological sample from a subject, and for correlating the presence of antibodies or levels of antibodies above a threshold level with the presence or severity of myasthenia gravis.

In some embodiments, the kits also contain negative and positive control samples for detection of antibodies. In some instances, the negative control samples are obtained from individuals or groups of individuals who do not have myasthenia gravis. In other instances, the positive control samples are obtained from individuals or groups of individuals who have myasthenia gravis. In some embodiments, the kits contain samples for the preparation of a titrated curve of antibodies in a sample, to assist in the evaluation of quantified levels of antibodies in a test biological sample.

E. Methods for Detecting or Determining the Severity of Myasthenia Gravis

In other aspects, the present invention provides methods for detecting or determining the severity of myasthenia gravis (MG) in a subject, the method comprising detecting in a biological sample from the subject the presence or absence of antibodies that bind to a peptide of the present invention or a plurality thereof, wherein the presence of antibodies that bind to the peptide or plurality thereof indicates the presence or an increased severity of MG. In some embodiments, the plurality of peptides comprises 2 or more (e.g., 2, 3, 4, 5, 6, 7, 8, 9, 10, or more) different peptides. In some instances the plurality of peptides comprises amino acid sequences set forth in SEQ ID NOS: 2, 3, 4, 6, 7, 23, 24, 25, 26, 27, or a combination thereof.

In some embodiments, the peptides bind to antibodies that bind to the MIR of an AChR. In some instances, the AChR is a nicotinic AChR. In certain instances, each of the different peptides binds to the same anti-MIR antibody, e.g., all of the different peptides bind to the same antibody that binds to the MIR of an AChR. In other instances, each of the different peptides binds to a different anti-MIR antibody.

In particular embodiments, the method further comprises obtaining the sample from the subject. With respect to the biological sample obtained from the subject, any fluid sample containing antibodies can be used. As non-limiting examples, the biological sample may be whole blood, serum, plasma, urine, saliva, or cerebrospinal fluid (CSF). One or more different bodily fluids can be evaluated for antibodies that specifically bind to the one or more peptides.

In some embodiments, the level or titer of the antibodies in the biological sample is compared to a threshold level or titer. A level or titer of the antibodies in the biological sample that is greater than the threshold level or titer indicates an increased probability that the subject has MG or has an increased severity of MG. Likewise, a level or titer of the antibodies in the biological sample that is less than the threshold level or titer does not indicate that the subject has MG or has an increased severity of MG.

The presence of the antibodies in the biological sample (e.g., fluid obtained from the subject) can be determined before or after the development of symptoms of MG. The presence of the antibodies may be determined once or more than once, as needed or desired. In some embodiments, the presence or absence of antibodies or the quantified levels of antibodies are evaluated every week, every month, several times a year (e.g., 2, 3, 4, 5, 6, 7, 8, 9, 10, 11, 12, or more times a year), or more or less often, as appropriate.

In some embodiments, presence of the antibodies is made without comparing the test sample (i.e., a biological sample from the subject) to a control sample. In other embodiments, the test sample is compared to a control. The control can be from the same individual at a different time point. In some instances, the control is obtained from the subject before developing symptoms of MG. In other instances, the control is obtained from the subject after developing symptoms of MG and/or after receiving treatment for MG.

The control can also be from a different individual with a known status for the presence of the antibodies or symptoms or diagnosis of MG. The control can also be a calculated value from a population of individuals with a known status for the presence of antibodies or symptoms or diagnosis of MG. The control may be a positive control or a negative control. In some embodiments, the control is a negative control from another individual or a population of individuals (e.g., an individual or population of individuals who do not have MG). If the known status of the control sample is negative for the antibodies, then a higher level of antibodies in the test sample than in the negative control sample indicates that the subject has MG or an increased severity of MG. A similar level of antibodies in the test sample compared to the negative control sample indicates that the subject does not have MG or an increased severity of MG.

In some embodiments, the control is a positive control from another individual or a population of individuals, or the control reflects a predetermined threshold level of antibodies. If the known status of the control sample is positive for antibodies, then a similar or higher level of antibodies in the test sample than in the positive control sample indicates that the subject has MG or an increased severity of MG. A lower level of antibodies in the test sample compared to the positive control sample indicates that the subject does not have MG or an increased severity of MG.

The differences between the control sample or value and the test sample need only be sufficient to be detected. In some embodiments, an increased level of antibodies in the test sample, and hence the presence of MG or increased severity of MG, is determined when the antibody levels are at least, e.g., 10%, 25%, 50%, 1-fold, 2-fold, 3-fold, 4-fold, or more in comparison to a negative or a prior-measured control.

The antibodies can be detected using any method known in the art. Exemplary methods include, without limitation, Western Blot, dot blot, enzyme-linked immunosorbent assay (ELISA), radioimmunoassay (RIA), immunoprecipitation, immunofluorescence, FACS analysis, electrochemiluminescence, and multiplex bead assays (e.g., using Luminex or fluorescent microbeads).

In some embodiments, the peptide or plurality thereof used to detect antibodies can be immobilized on a solid support. The solid support can be, for example, a multiwell plate, a microarray, a chip, a bead, a porous strip, or a nitrocellulose filter. In some instances, the bead comprises chitin. The immobilization can be via covalent or non-covalent binding. In some embodiments, the immobilization is through a capture antibody that specifically binds to the target epitope.

For detection of antibodies, a sample can be incubated with one or more of the peptides described herein under conditions (e.g., time, temperature, concentration of sample) sufficient to allow specific binding of antibodies to the peptides. The one or more peptides can be bound to a solid support. For example, the one or more peptides can be exposed to a sample for about 0.5, 1.0, 1.5, 2.0, 2.5, 3.0 hours, or overnight, about 8, 10, 12, 14, or 16 hours. However, incubation time can be more or less depending on, e.g., the composition of the one or more peptides, the composition of the one or more antibodies, the dilution of the sample, and the temperature for incubation. Incubations are usually carried out at room temperature (about 25° C.) or at biological temperature (about 37° C.), and can be carried out in a refrigerator (about 4° C.). Washing to remove unbound sample before addition of a secondary antibody is carried according to known immunoassay methods.

Labeled secondary antibodies are generally used to detect antibodies in a sample that have bound to one or more of the peptides described herein. Secondary antibodies bind to the constant or "C" regions of different classes or isotypes of immunoglobulins IgM, IgD, IgG, IgA, and IgE. Usually, a secondary antibody against an IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (e.g., fluorescein, phycoerythrin, quantum dot, Luminex bead, fluorescent bead), an enzyme (e.g., peroxidase, alkaline phosphatase), a radioisotope (e.g., $^{3}H$, $^{32}P$, $^{125}I$) or a chemiluminescent moiety. Labeling signals can be amplified using a complex of biotin and a biotin binding moiety (e.g., avidin, streptavidin, neutravidin). Fluorescently labeled anti-human IgG antibodies are commercially available from Molecular Probes, Eugene, Oreg. Enzyme-labeled anti-human IgG antibodies are commercially available from Sigma-Aldrich, St. Louis, Mo. and Chemicon, Temecula, Calif.

The method of detection of the presence or absence, or differential presence, of antibodies in a sample will correspond with the choice of label of the secondary antibody. For example, if one or more of the peptides described herein are transferred onto a membrane substrate suitable for immunoblotting, the detectable signals (i.e., blots) can be quantified using a digital imager if enzymatic labeling is used or an x-ray film developer if radioisotope labeling is used. In another example, if one or more of the peptides described herein are transferred to a multi-well plate, the detectable signals can be quantified using an automated plate reader capable of detecting and quantifying fluorescent, chemiluminescent, and/or colorimetric signals. Such methods of detection are well known in the art.

General immunoassay techniques are well known in the art. Guidance for optimization of parameters can be found in, for example, Wu, Quantitative Immunoassay: A Practical Guide for Assay Establishment, Troubleshooting, and Clinical Application, 2000, AACC Press; Principles and Practice of Immunoassay, Price and Newman, eds., 1997, Groves Dictionaries, Inc.; The Immunoassay Handbook, Wild, ed., 2005, Elsevier Science Ltd.; Ghindilis, Pavlov and Atanassov, Immunoassay Methods and Protocols, 2003, Humana Press; Harlow and Lane, Using Antibodies: A Laboratory Manual, 1998, Cold Spring Harbor Laboratory Press; and Immunoassay Automation: An Updated Guide to Systems, Chan, ed., 1996, Academic Press.

In certain embodiments, the presence or increased presence of antibodies is indicated by a detectable signal (e.g., a blot, fluorescence, chemiluminescence, color, radioactivity) in an immunoassay, where the biological sample from the subject is contacted with one or more of the peptides described herein. This detectable signal can be compared to the signal from a control sample or to a threshold value. In some embodiments, increased presence is detected, and the presence or increased severity of MG is indicated, when the detectable signal of antibodies in the test sample is at least about 10%, 20%, 30%, 50%, 75% greater in comparison to the signal of antibodies in the control sample or the predetermined threshold value. In some embodiments, an increased presence is detected, and the presence or increased severity of MG is indicated, when the detectable signal of antibodies in the test sample is at least about 1-fold, 2-fold, 3-fold, 4-fold or more, greater in comparison to the signal of antibodies in the control sample or the predetermined threshold value.

In some embodiments, the results of the antibody determinations are recorded in a tangible medium. For example, the results of the present diagnostic assays (e.g., the observation of the presence or increased presence of antibodies) and the diagnosis of whether or not there is an increased severity or the presence of MG can be recorded, e.g., on paper or on electronic media (e.g., audio tape, a computer disk, a CD, a flash drive, etc.).

In other embodiments, the methods further comprise the step of providing the diagnosis to the patient (i.e., the subject).

F. Methods for Preventing or Treating Myasthenia Gravis

In another aspect, the invention provides methods for preventing or treating myasthenia gravis (MG) in a subject, the method comprising administering to the subject a therapeutically effective amount of a peptide of the present invention or a plurality thereof, wherein the peptide or plurality thereof binds to antibodies circulating in the subject to form neutralizing complexes, thereby preventing or treating MG. In particular embodiments, the circulating antibodies bind to the main immunogenic region (MIR) of an acetylcholine receptor (AChR). In some instances, the AChR is a nicotinic AChR. In particular instances, the peptide or plurality thereof binds to and blocks an antibody combining site.

In some embodiments, the plurality of peptides comprises 2 or more (e.g., 2, 3, 4, 5, 6, 7, 8, 9, 10, or more) different peptides. In some instances the plurality of peptides comprises amino acid sequences set forth in SEQ ID NOS: 2, 3, 4, 6, 7, 23, 24, 25, 26, 27, or a combination thereof. In certain instances, each of the different peptides binds to the same anti-MIR antibody, e.g., all of the different peptides bind to the same antibody that binds to the MIR of an AChR. In other instances, each of the different peptides binds to a different anti-MIR antibody.

In particular embodiments, the peptides or plurality thereof that are administered to the subject further comprise one or more antibodies or fragments thereof that are conjugated to the peptide or plurality thereof. The antibodies or fragments thereof can comprise one or more light chains, heavy chains, fragments thereof, or combinations thereof. Any fragment or combination of heavy chain domains or regions can be conjugated to the peptide(s), including the variable domain ($V_H$), hinge region, and constant ($C_H1$, $C_H2$, and $C_H3$) domains. In particular instances, the hinge region of the antibody fragment is conjugated to the C-terminal end of the peptide. In other particular instances, the antibody fragment comprises the hinge region, $C_H2$ domain, and $C_H3$ domain of the heavy chain. In some instances, the one or antibodies or fragments thereof comprise one or more Fc domains, one or more Fab domains, or a combination thereof.

Conjugating antibody fragments to peptides of the present invention (e.g., conjugating an IgG heavy chain fragment comprising the hinge region and $C_H2$ and $C_H3$ domains to a peptide of the present invention) can be useful for extending the bioavailability of the peptides. In addition, as discussed in Example 2 and FIG. 14B, peptide-antibody fragment conjugates are useful for inactivating and/or reducing the number of B-cells that are involved in the production of pathogenic anti-MIR antibodies, e.g., by complement activation, antibody-dependent cell-mediated toxicity, induced apoptosis, or a combination thereof.

In some embodiments, the subject being treated is exhibiting one or more symptoms of MG. In some instances, treating the subject results in a decrease or abolishment of one or more symptoms of MG.

In some embodiments, biological fluid containing antibodies can be removed from the subject and contacted with one or more of the peptides described herein. In other embodiments, one or more of the peptides described herein can be administered to the subject to block the binding between the antibodies and their AChR targets, thereby neutralizing the antibodies, and the neutralized complexes present in the biological fluid are removed using an extracorporeal therapy, such as affinity plasmapheresis. As non-limiting examples, the peptide of the present invention or plurality thereof can be administered to the subject intravenously, intramuscularly, intrathecally, or a combination thereof.

In some embodiments, biological fluid from the subject is contacted with one or more of the peptides immobilized on a solid support. The solid support can be, for example, a multiwell plate, an ELISA plate, a microarray, a chip, a bead, a column, a porous strip, a membrane, or a nitrocellulose filter. The bead can comprise chitin. The immobilization can be via covalent or non-covalent binding. In some embodiments, the immobilization is through a capture antibody that specifically binds to the target peptide epitope. The peptide(s) attached to the solid support form a stationary phase that captures the antibodies in the biological fluid, allowing the biological fluid with reduced or eliminated levels of pathogenic anti-AChR or anti-MIR antibodies to be separated from the solid support, i.e., as the mobile phase, and returned to the subject.

In some embodiments, the biological fluid that is processed ex vivo is plasma, and the antibodies are removed by plasmapheresis, a process well known in the art. The plasma is contacted with a solid support with one or more immobilized peptides. Antibodies in the plasma bind to the immobilized peptides. Plasma with reduced or eliminated levels of antibodies is then returned to the subject.

The ex vivo removal of antibodies can be carried out on a subject before or after developing symptoms or receiving a diagnosis of MG. The process of ex vivo antibody removal can be performed one, two, three, four, or more times, as needed to eliminate or reduce the antibodies from the subject. Ex vivo removal of the antibodies can be performed daily, weekly, bi-weekly, monthly, bi-monthly, as appropriate. In some embodiments, the levels of antibodies in the subject are monitored and ex vivo antibody removal performed if the presence of antibodies are above a predetermined threshold level. Ex vivo antibody removal can be carried out over a time period of a 1, 2, 3, 4, 5, 10, 12, 15, 20, 30, 40, or 50 weeks, or longer or shorter, as appropriate. For example, ex vivo removal of antibodies can be discontinued if the level of antibodies falls below a predetermined threshold level.

IV. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1. Creation of Peptides for Binding Pathogenic Anti-MIR Antibodies and Treating Myasthenia Gravis This example describes the creation of peptides that bind to antibodies against that main immunogenic region (MIR) of the nicotinic acetylcholine receptor (AChR) and shows that some of the peptides can bind to pathogenic anti-MIR antibodies in serum samples obtained from human myasthenia gravis (MG) patients.

Introduction

The nicotinic acetylcholine receptor (AChR) main immunogenic region (MIR) is the target of many pathogenic antibodies (Abs) in patients with autoimmune myasthenia gravis (MG). This disease results in the destruction of the postsynaptic membrane folded architecture and concomitant loss of AChR density (1,2). Electron micrographs of single chain Fv and/or Fab fragments of monoclonal Ab (mAb) 35 bound to 2-D crystalline arrays of *Torpedo* AChRs (TAChRs) reveal that the MIR is on top of the extracellular region of each of the two AChR alpha subunits (3). The MIR consists of a group of overlapping epitopes of mAbs raised in rats against the *Torpedo* and/or *Electrophorus* electric organ AChR (4-6). Many of these mAbs cross-react with the AChRs of many different species, including humans (7,8). The binding of mAb 132A, an anti-TAChR mAb, is competitively inhibited by mAb 35 (9), the classic anti-MIR directed mAb. The MIR has stimulated considerable interest, as a substantial fraction of the mAbs raised against the *Torpedo* or *Electrophorus* electric organ AChR are directed to this region and mutually inhibit one another's binding (10,11). In addition, several of these mAbs seem to be particularly effective in passively transferring myasthenic symptoms to naïve rats upon intravenous injection. The region also presents the conundrum of being present in the folded assembled AChR, but frequently not detected by the mAbs binding to a particular AChR subunit in Western blots. However, mAb 132A does bind to the TAChR alpha subunit in Western blots and has consequently proved quite useful in mapping its epitope to three non-contiguous segments of the TAChR alpha subunit: α(1-12), α(65-79), and α(110-115) (9). Locating these segments on Unwin's 4 Å 3-D model of the TAChR (12), indicates their close proximity to one another (FIG. 1). α(1-12) is part of the N-terminal α-helix, and it sits next to α(65-79), the core segment (13) of the MIR. α(65-79) consists of a short helix, α(69-74), nestled between two coil/β-strand legs, α(65-68) and α(75-79). α(65-79) is draped over the α(110-115), a β-turn (12). α(1-12) and α(65-79) appear to function as the epitope recognition site, while α(110-115) appears to serve as a structural anchor stabilizing the α(1-12)/α(65-79) complex (9).

Because of the pathogenic potential of Abs-directed against the MIR in an experimental autoimmune myasthenia gravis (EAMG) and human MG sera, a *Torpedo* 39 amino acid (aa) MIR peptide mimic (39MIR) of the *Torpedo* MIR was synthesized and characterized. The mimic consists of three non-contiguous segments of the AChR that are joined by flexible GGGS and GS amino acid linkers, and is fused to the amino terminus of an intein-chitin binding domain (IChBD) (14). This mimic binds mAb 132A with a $K_d$ of $2.1\times10^{-10}$ M, in contrast to the $K_d$ of the complex of 132A with the AChR itself ($3.4\times10^{-10}$ M). This peptide construct was also able to adsorb all of the MIR directed Abs in EAMG sera that block the binding of biotinylated mAb 132A to the *Torpedo* AChR (14). Another fusion protein has been engineered with the 39MIR C-terminus linked to the N-terminus of the hinge of human and rat IgG antibody heavy chains (15). These constructs can also be used therapeutically to neutralize MIR directed Abs in EAMG sera or a human homolog can be used to neutralize MIR-directed Abs in MG sera.

Mammalian 39MIR homologs have also been produced. Initial attempts at making a mammalian MIR mimic involved putting the rat/mouse and human sequences in the corresponding positions of the *Torpedo* 39MIR that were recognized by anti-TAChR MIR mAbs and anti-TAChR MIR Abs in EAMG serum. The rat/mouse and human 39MIRs incorporate the same three segments of the rat/human alpha subunit as those from the *Torpedo* alpha subunit: α(1-12), α(65-79), and α(110-115). Like the *Torpedo* peptide, they are linked by flexible GGGS and GS linkers. The peptide homologs were fused to an IChBD tag and affinity purified from disrupted *E. coli* by adsorption onto chitin beads. The human homolog contains eight amino acids that are different from the *Torpedo* 39MIR sequence while the rat homologue contains only seven (FIG. 2).

The AChR MIR is evolutionarily conserved between *Torpedo* and mammals. The *Torpedo* and human alpha subunits have 80% sequence similarity (16). There is also 76% sequence similarity between the human and *Torpedo* MIR mimic segments: α(1-12), α(65-79), and α(110-115). Some MIR-directed mAbs raised against electric organ AChR cross react with AChRs from other species (11). For example, mAb 35 cross-reacts with receptors from *Torpedo*, bovines, and humans (8, 17, 18). In addition, mAb 132A, raised against *Torpedo* electric organ AChR in rats, binds to the *Torpedo* MIR and stains the neuromuscular junction (NMJ) of mouse and human tissue, and causes disease in naive rats when injected (7,17). Additionally, EAMG rats produce Abs that bind to the rat MIR (17-20).

The human 39MIR does not bind to mAbs 35 or 132A despite evidence that both mAbs recognize human and rat/mouse AChR (4,7). To identify the amino acids responsible for the loss of mAb binding, amino acid substitutions were made at positions that differ between the *Torpedo* and human 39MIRs, and the effect of the substitutions on the binding of anti-MIR mAbs 35, 132A, 198, 334, and 371A was tested. Two *Torpedo*/human chimeric 39MIRs were designed that exhibit binding of mAbs 35, 132A, and mAb 198. In addition, the chimeric mimics also bind Abs from EAMG serum and human MG sera, and can be used in the production of a pseudo anti-idiotype Ab construct with the human and rat IgG heavy chains that will not only neutralize anti-MIR Abs, but also target the memory B-cells involved in the production of pathogenic anti-MIR Abs.

Results

1. The Human 39MIR Peptide Mimic is Recognized by mAb 198 but not mAbs 35 and 132A.

Figure 3:
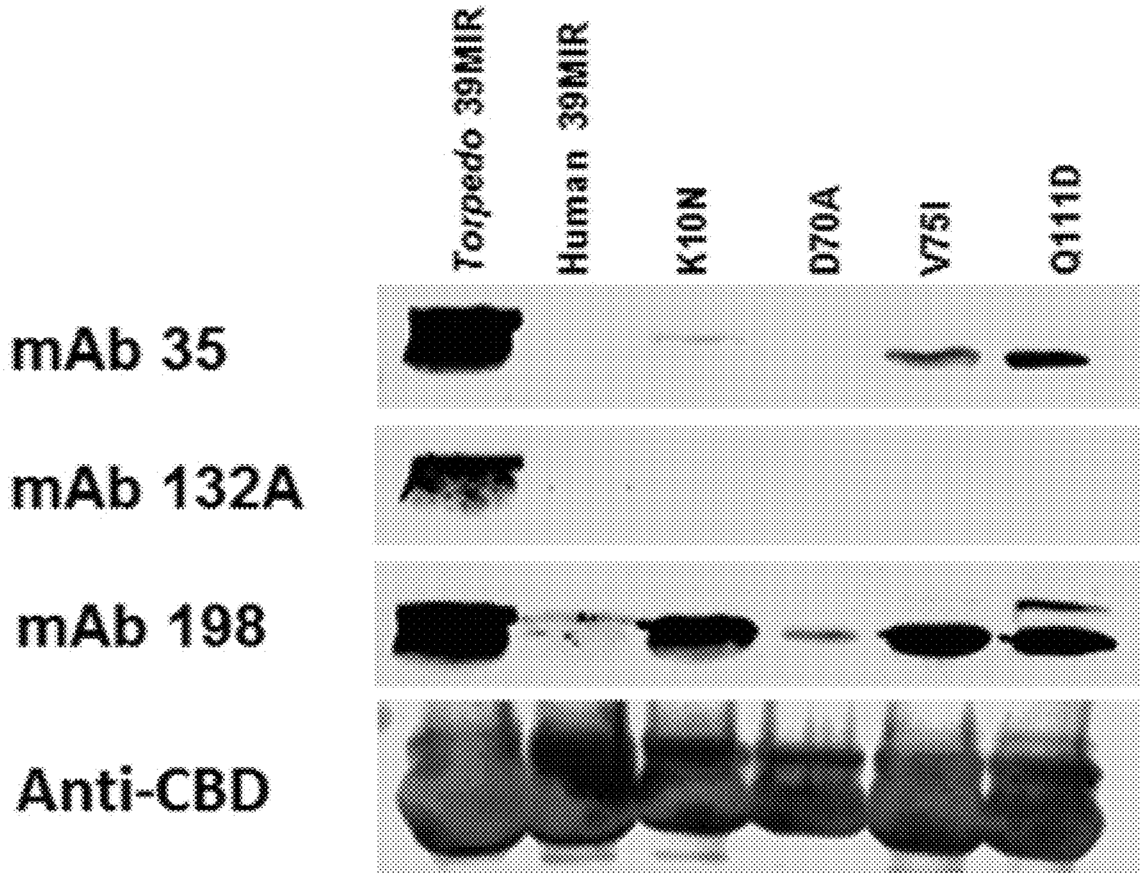
FIG. 3 shows a Western blot illustrating binding between four monoclonal antibodies (mAb 35, mAb 132A, mAb 198, and an anti-chitin-binding domain mAb) and six peptide-intein-chitin-binding domain (IChBD) fusion proteins (the six peptides being *Torpedo* 39MIR (SEQ ID NO:9), human 39MIR (SEQ ID NO:8), K10N human 39MIR mutant (SEQ ID NO:19), D70A human 39MIR mutant (SEQ ID NO:20), V75I human 39MIR mutant (SEQ ID NO:21), and Q111D human 39MIR mutant (SEQ ID NO:22)). Chitin beads adsorbed with peptide-IChBD fusion proteins were run on an SDS-PAGE gel and transferred to a nitrocellulose membrane and assayed with the four mAbs.

The *Torpedo* (SEQ ID NO:9) and human (SEQ ID NO:8) 39MIRs were made by joining the α(1-12), α(65-79), and α(110-115) segments of their respective a subunits with GS linkers. These two MIR mimics were expressed in *E. coli* as fusion proteins with an IChBD tag to permit peptide collection on chitin beads. These two peptides differ from each other by eight amino acids (FIG. 2). Both mimics were probed with mAb 198. mAb 198, which was derived from rats that had been immunized with human muscle AChR, is a MIR-directed mAb that binds mammalian as well as *Torpedo* MIR (13,21). It was also able to passively transfer EAMG to rats and binds to both native assembled AChR and to α-subunit fragments in Western blots (22,23). mAb 198 binds to the *Torpedo* and human MIR peptide mimics in Western blots (FIG. 3). However, mAb 198 binds to the *Torpedo* mimic about 50 times more strongly than to the human MIR mimic (FIG. 3).

Referring to FIG. 3 again, it can be seen that the human 39MIR is not recognized by mAbs 35 or 132A at all in Western blots. However, both mAbs bind to the assembled *Torpedo* AChR and to the AChR of a variety of species including humans, (7) and transfer disease to naïve rats. This result suggests that perhaps the human 39MIR mimic folds slightly differently from the *Torpedo* 39MIR in the Western blot format, and slightly differently than the human MIR assembled in the AChR. Support for this idea also comes from a comparison of the structures of the three MIR segments from the *Torpedo* 39MIR mimic culled from the 4 Å AChR structure (12) to the three segments culled from the 1.97 Å X-ray structure of the mouse alpha subunit extracellular domain in complex with α-bungarotoxin. The mouse 39MIR has seven of the eight amino acid substitutions in common with the human 39MIR from the *Torpedo*. Despite compact folding differences, differences can also be observed in the placement of specific side chains in the two constructs. For example, tyrosine 72 prominently protrudes from the middle of a segment of the *Torpedo* MIR, whereas in the mouse MIR the corresponding residue in the corresponding segment is completely buried.

2. Effects of Amino Acid Substitutions Between *Torpedo* and Human 39MIR.

To explore the effects of individual amino acid substitutions between the *Torpedo* and the human AChR MIR mimics, eight peptides were prepared, each with an amino acid substituted from the human sequence into the *Torpedo* sequence. The single amino acid substitutions in the *Torpedo* MIR were: N10K (SEQ ID NO:11), L12F (SEQ ID NO:12), R66K (SEQ ID NO:13), A70D (SEQ ID NO:14), I75V (SEQ ID NO:15), R79H (SEQ ID NO:16), D111Q (SEQ ID NO:17), and K115H (SEQ ID NO:18). Sequence alignments are shown in FIG. 4. These peptides, each attached to an IChBD tag, were collected on chitin beads from the *E. coli* extract, and run on an SDS-PAGE gel and transferred to nitrocellulose for staining with the five mAbs in the Western blots displayed in FIG. 5. The effects on binding are shown in Table 1.

mAbs 35, 132A, and 334 are all anti-electric organ AChR MIR-directed mAbs. mAb 198, raised against purified human AChR, bound to mammalian and *Torpedo* MIR to a similar degree as to MIR mimics (14, 22, 23). mAb 147G, a rat anti-fluorescein mAb, served as the negative control and binds to nothing in the blots.

Figure 5:
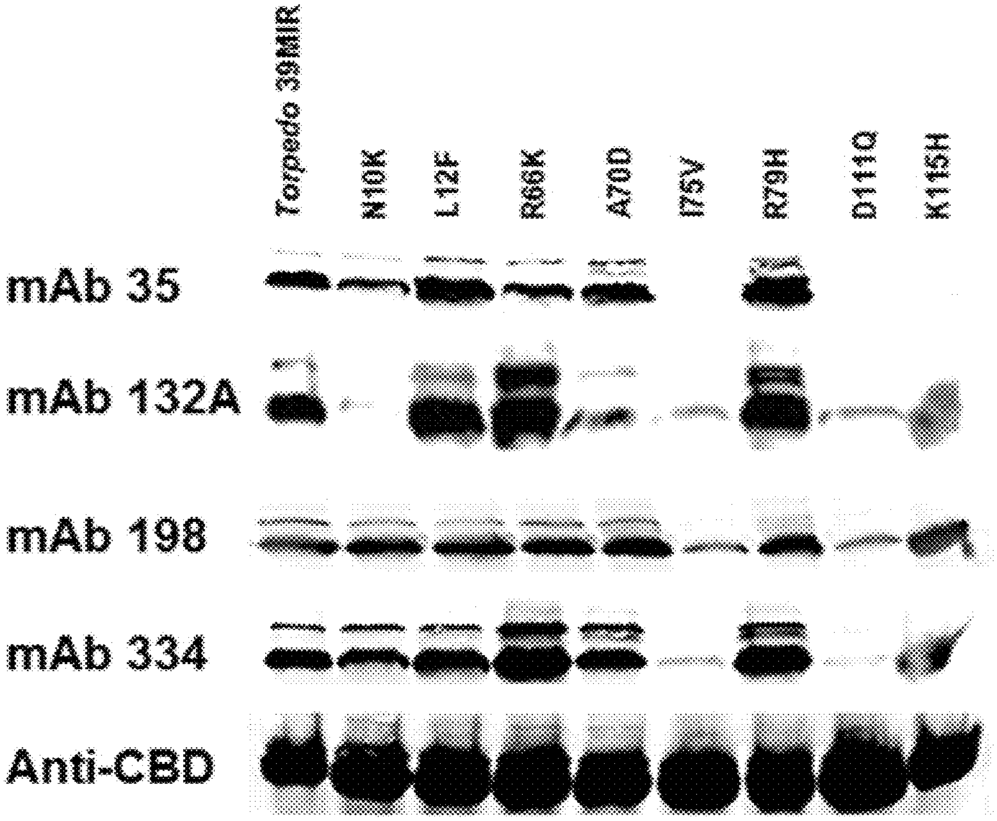
FIG. 5 shows a Western blot illustrating binding between five monoclonal antibodies (mAb 35, mAb 132A, mAb 198, mAb 334, and an anti-chitin-binding domain mAb) and nine peptide-IChBD fusion proteins (the nine peptides being *Torpedo* 39MIR (SEQ ID NO:9) and eight *Torpedo* 39MIR mutants: N10K (SEQ ID NO:11), L12F (SEQ ID NO:12), R66K (SEQ ID NO:13), A70D (SEQ ID NO:14), I75V (SEQ ID NO:15), R79H (SEQ ID NO:16), D111Q (SEQ ID NO:17), and K115H (SEQ ID NO:18)). Chitin beads adsorbed with peptide-IChBD fusion proteins were run on an SDS-PAGE gel and transferred to a nitrocellulose membrane and assayed with the five mAbs.

In the FIG. 5 Western blots (also see Table 1), it can be seen that mAb 35 did not bind to the I75V, D111Q or K115H peptides. mAb 35 exhibited improved binding to the L12F (1.42×) and R79H (1.91×) peptides and decreased binding to N10K (0.29×) and R66K (0.62×) peptides, relative to binding to the *Torpedo* 39MIR. Binding to A70D (0.93×) remained relatively unchanged.

mAb 132A exhibited substantially weakened binding to the N10K (0.03×), A70D (0.20×), I75V (0.07×), D111Q (0.07×) and K115H (0.40×) peptides, and stronger binding to the R66K (1.55×) and R79H (1.65×) peptides, relative to binding of mAb 132A to the *Torpedo* 39MIR (Table 1). Binding to L12F (1.10×) remained relatively unchanged.

mAb 198 exhibited decreased binding to the N10K (0.82×), I75V (0.16×) and D111Q (0.16×) peptides, and fairly uniform binding to the other five chimeric point mutated peptides (Table 1).

mAb 334 exhibited weakened binding to the N10K (0.59×), L12F (0.88×), I75V (0.03×), D111Q (0.02×), and K115H (0.42×) peptides, stronger binding to the R66K (2.75×) and R79H (2.40×) peptides, and unchanged binding to A70D (1.04×) peptides (Table 1). mAb 147G, the negative control, did not bind to any of the peptides.

The N10K, I75V and D111Q substitutions resulted in the most consistent impairment of MIR-directed mAb binding. The A70D substitution primarily affected the binding of mAb 132A, while not affecting the binding of the other mAbs. The K115H substitution also impaired binding of mAb 35, 132A, and mAb 334, with the mAb 35 binding being completely abolished.

3. Optimized *Torpedo*/Human Chimeric 39MIR Peptide.

The human 39MIR peptide was point mutated to induce amino acid substitutions corresponding to the analogous *Torpedo* sequence at four positions, resulting in the K10N, D70A, V75I, and Q111D peptides (SEQ ID NOS:19, 20, 21, and 22, respectively), in an attempt to identify the contribution of these amino acids to mAb binding and to improve the binding of electric organ mAbs 132A and 35 (FIG. 6). Three of the single point mutated peptides, (K10N (0.01), V75I (0.03), and Q111D (0.06)) of the human 39MIR restored mAb 35 binding, although to very low levels compared to the *Torpedo* 39MIR peptide. The D70A mutated human 39MIR failed to restore mAb 35 binding to the human 39MIR. None of these mutant peptides restored mAb 132 binding. The human 39MIR was originally recognized by mAb 198. However, the K10N (13×), V75I (40×), and Q111D (35.7×) mutations greatly improved mAb 198 binding compared to its binding to the human 39MIR. mAb 198 binding to the D70A mutant was comparable to binding to human 39MIR. Taken together, these single point mutations are not responsible for the loss of mAb binding. It is more likely that a combination of all or a few of the mutations are responsible for the loss of mAb binding.

Figure 7:
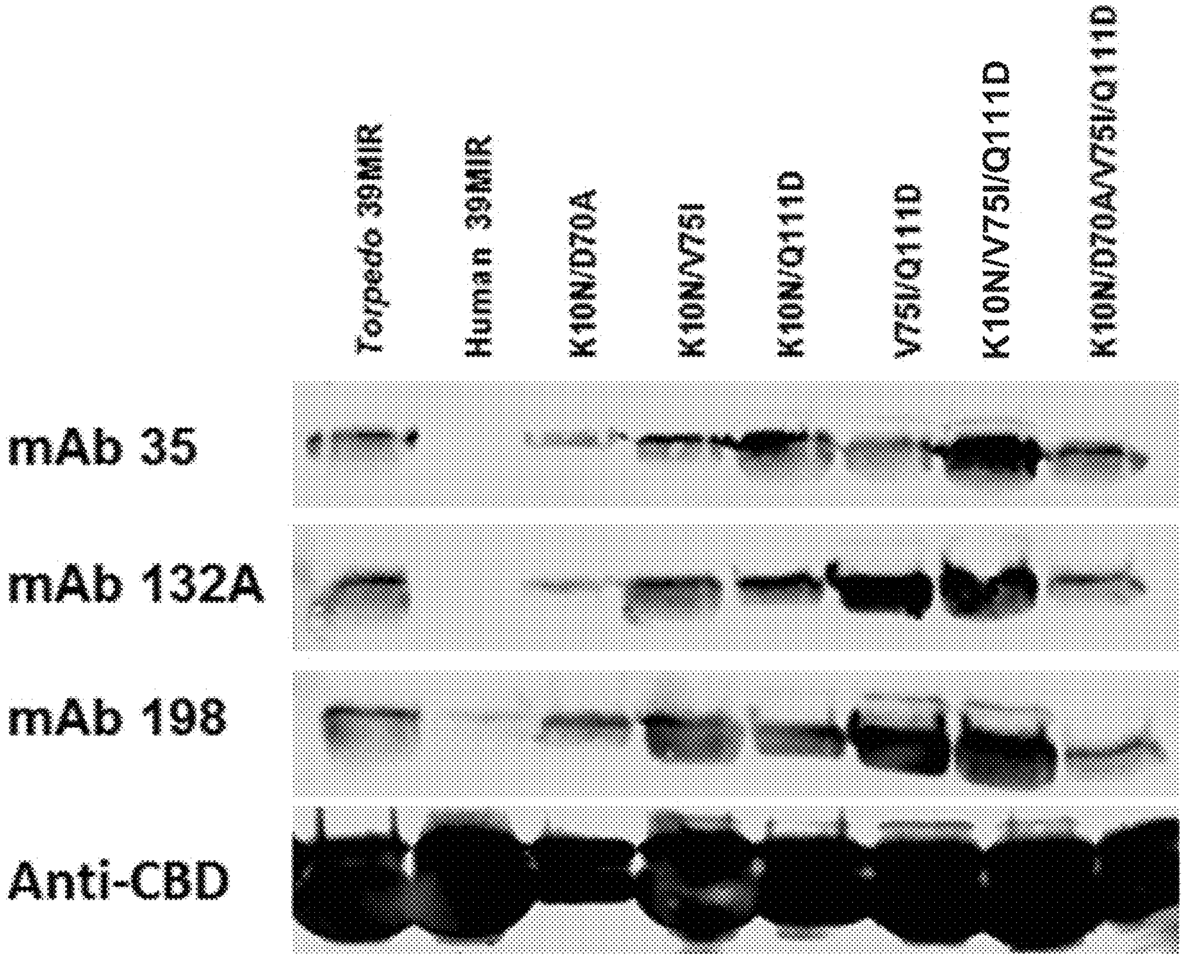
FIG. 7 shows a Western blot illustrating binding between four monoclonal antibodies (mAb 35, mAb 132A, mAb 198, and an anti-chitin-binding domain mAb) and eight -IChBD fusion proteins (the eight peptides being *Torpedo* 39MIR (SEQ ID NO:9), human 39MIR (SEQ ID NO:8), K10N/D70A human 39MIR double mutant (SEQ ID NO:23), K10N/V75I human 39MIR double mutant (SEQ ID NO:24), K10N/Q111D human 39MIR double mutant (SEQ ID NO25:), V75I/Q111D human 39MIR double mutant (SEQ ID NO:5), K10N/V75I/Q111D human 39MIR triple mutant (SEQ ID NO:26), and K10N/D70A/V75I/Q111D human 39MIR quadruple mutant (SEQ ID NO:27)). Chitin beads adsorbed with peptide-IChBD fusion proteins were run on an SDS-PAGE gel and transferred to a nitrocellulose membrane and assayed with the four mAbs.

Various double mutants were also tested for binding to the MIR-directed mAbs. The K10N/D70A (SEQ ID NO:23), K10N/V75I (SEQ ID NO:24), K10N/Q111D (SEQ ID NO:25), and V75I/Q111D (SEQ ID NO:5) mutants all restored binding with mAb 35, 132A, and mAb198 (FIG. 7 and Table 2).

A K10N/N75I/Q111D mutant (SEQ ID NO:26) was made to test the contribution of the D amino acid at position 70. Whereas the human 39MIR was not recognized by mAb 35 or 132A, this triple mutant exhibited improved binding to both mAb 35 (2.97×) and 132A (2.46×) when compared to the *Torpedo* 39 MIR. The triple mutant also bound to mAb 198 (2.52×) better than the *Torpedo* 39 MIR, resulting in a 28× improvement compared to the human 39MIR. Surprisingly, this triple mutant was better at binding the mAbs than a mutant peptide containing all four (i.e., K10N, D70A, V75I, and Q111D) mutations.

Like the triple mutant, the K10N/D70A/V75I/Q111D mutant (SEQ ID NO:27) restored binding to mAb 35 (1.70×) and mAb 132A (0.99×). It also improved on mAb 198 recognition, improving binding by 11× comparable to the human 39MIR (FIG. 7). The K10N/N75I/Q111D triple mutant appeared to be the peptide most optimized for binding to the MIR-directed mAbs 35, 132A, and 198. Results are summarized in Table 2.

4. Peptide Recognition of Antibodies in Human MG Sera.

Figure 11:
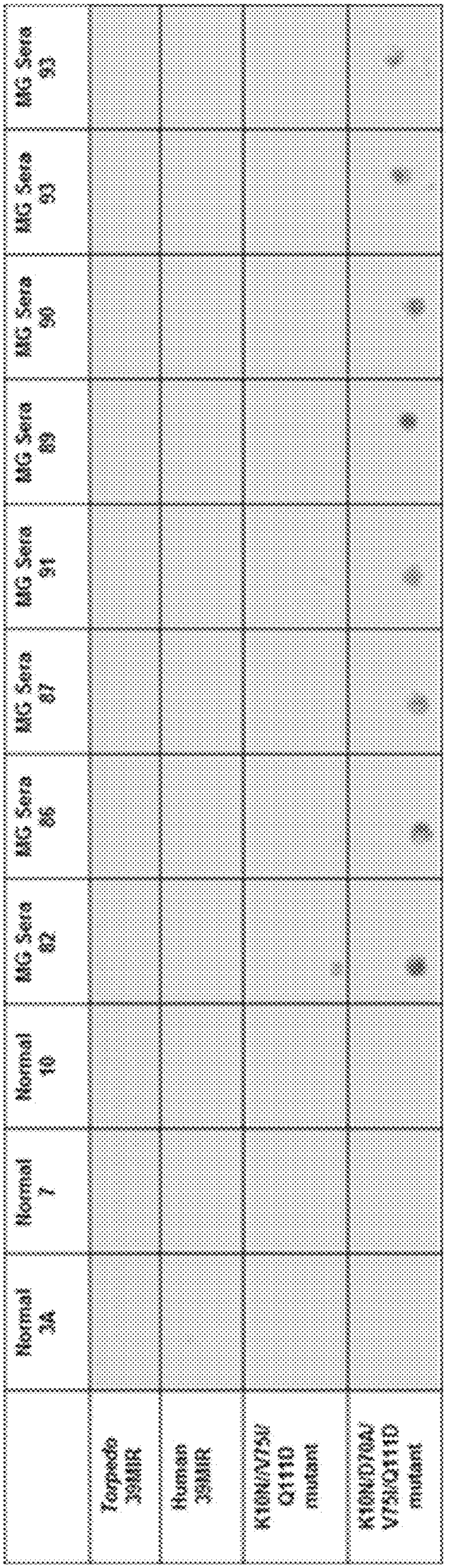
FIG. 11 shows a dot blot of four peptides against various human serum samples. Sample were obtained from either normal subjects (i.e., without a diagnosis of myasthenia gravis (MG)) or subjects diagnosed with MG. Samples were contacted with the *Torpedo* 39MIR peptide (SEQ ID NO:9), the human 39MIR peptide (SEQ ID NO:8), the K10N/V75I/Q11D human 39MIR triple mutant (SEQ ID NO:26), or the K10N/D70A/V75I/Q111D human 39MIR quadruple mutant (SEQ ID NO:27).

His-tagged variants of the *Torpedo* 39MIR, human 39MIR, K10/V75I/Q111D triple mutant, and K10N/D70A/V75I/Q111D quadruple mutant peptides were expressed and probed for binding to antibodies in human MG serum samples. The peptides were dot-blotted onto a membrane and probed for binding to antibodies in our human MG serum library. The *Torpedo* 39MIR and human 39MIR peptides did not bind any antibodies in the MG serum samples. However, both K10N/N75I/Q111D and K10N/D70A/V75I/Q111D His-tagged peptides bound antibodies in the human sera. Surprisingly, the triple mutant (SEQ ID NO:26), which had higher affinity to our pathogenic mAb library, only bound antibodies in one MG serum sample, while the quadruple mutant peptide (SEQ ID NO:27) was able to bind antibodies in all of our human MG serum samples. None of the His-tagged peptides bound any antibodies in normal human serum samples (FIG. 11). Although the triple mutant peptide (SEQ ID NO:26) bound better overall to mAb 35, mAb 132A, and mAb 198, the quadruple mutant peptide (SEQ ID NO:27) was better for binding antibodies in MG sera. That the peptides are able to bind pathogenic MIR-directed mAbs in MG serum samples shows that they have therapeutic potential for the treatment of MG.

Figure 8A:
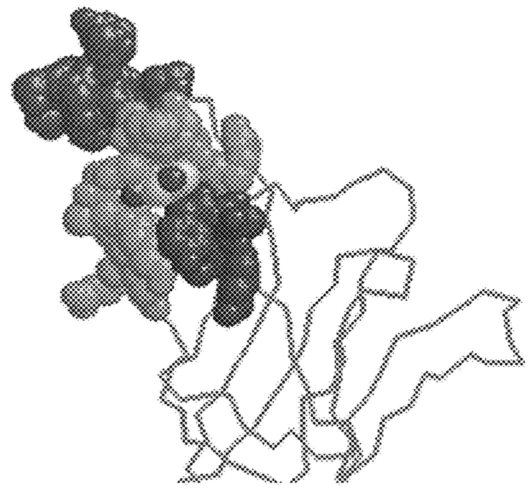
FIGS. 8A and 8B show a comparison of the *Torpedo* and mouse MIRs.
Figure 8B:
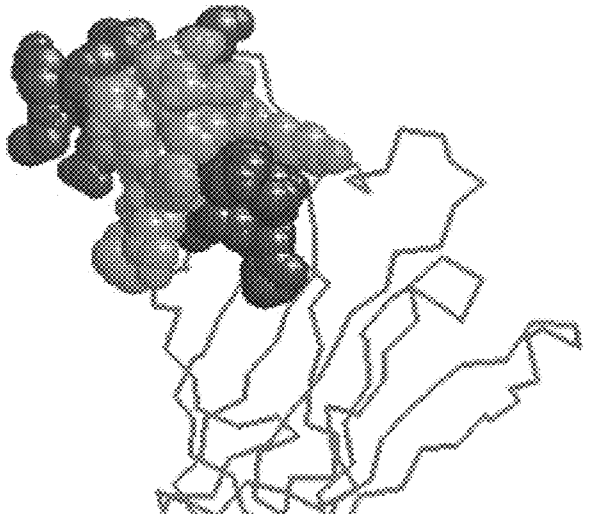
Figure 9A:
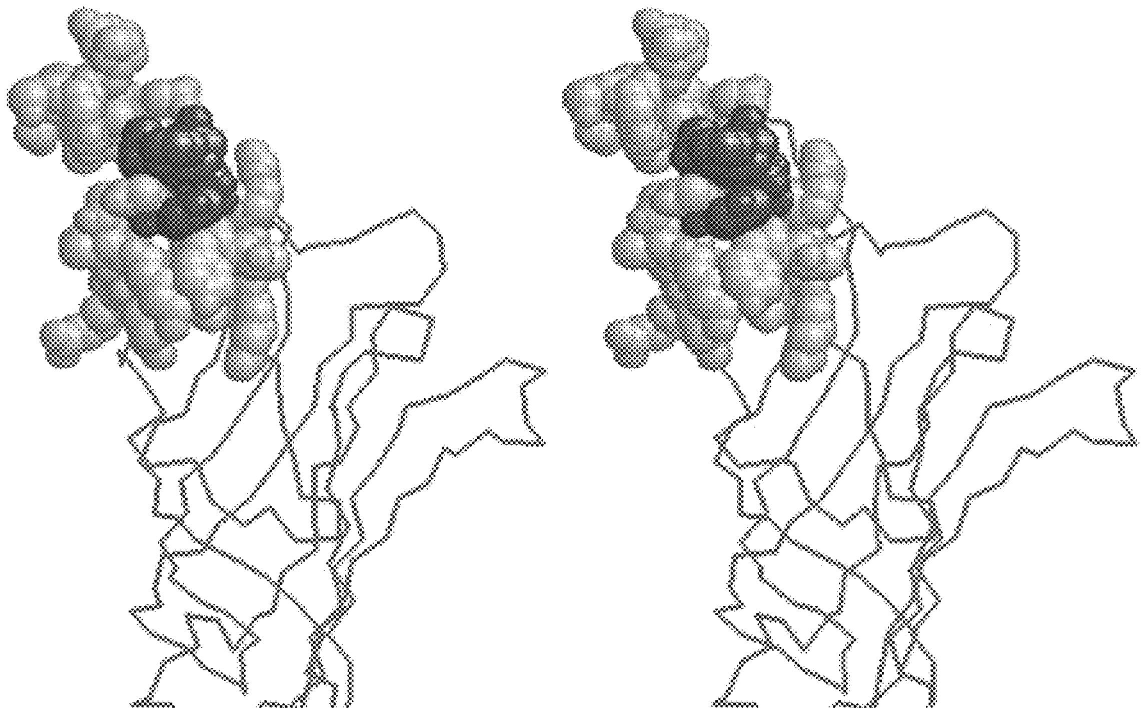
FIGS. 9A and 9B show a comparison of the *Torpedo* and mouse core MIRs. Cores correspond to amino acids 67-76 and are shown with dark shading.
Figure 9B:
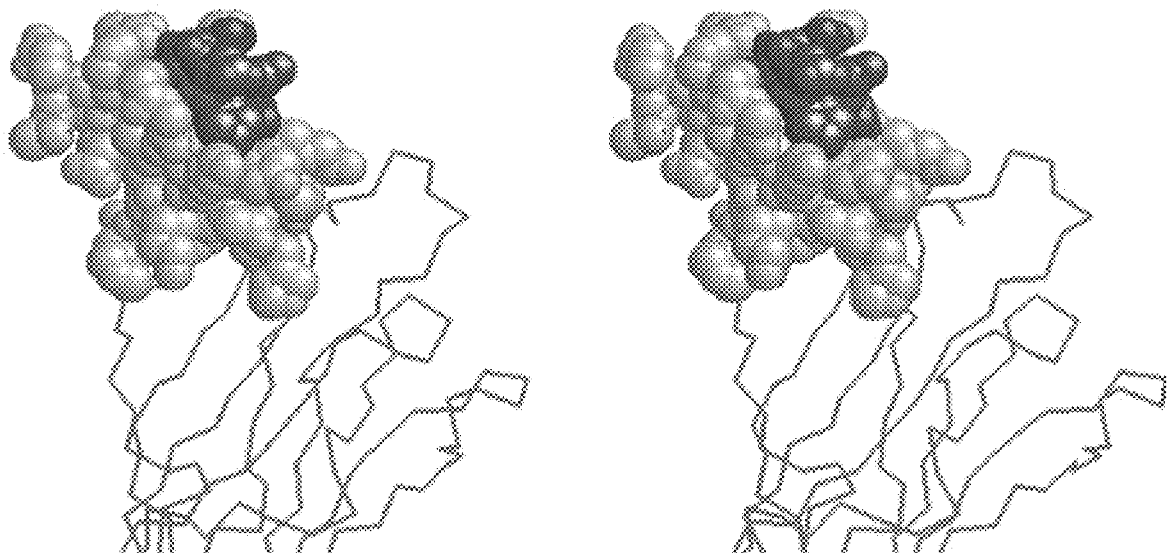
Figure 10A:
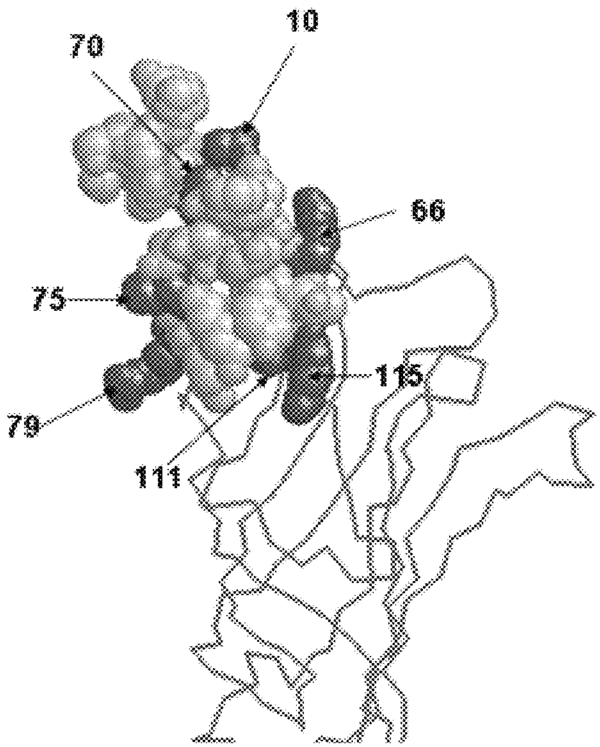
FIGS. 10A and 10B show a comparison of the *Torpedo* and MIRs, denoting locations of amino acids that differ between *Torpedo* and mouse (labeled and shown with dark shading).
Figure 10B:
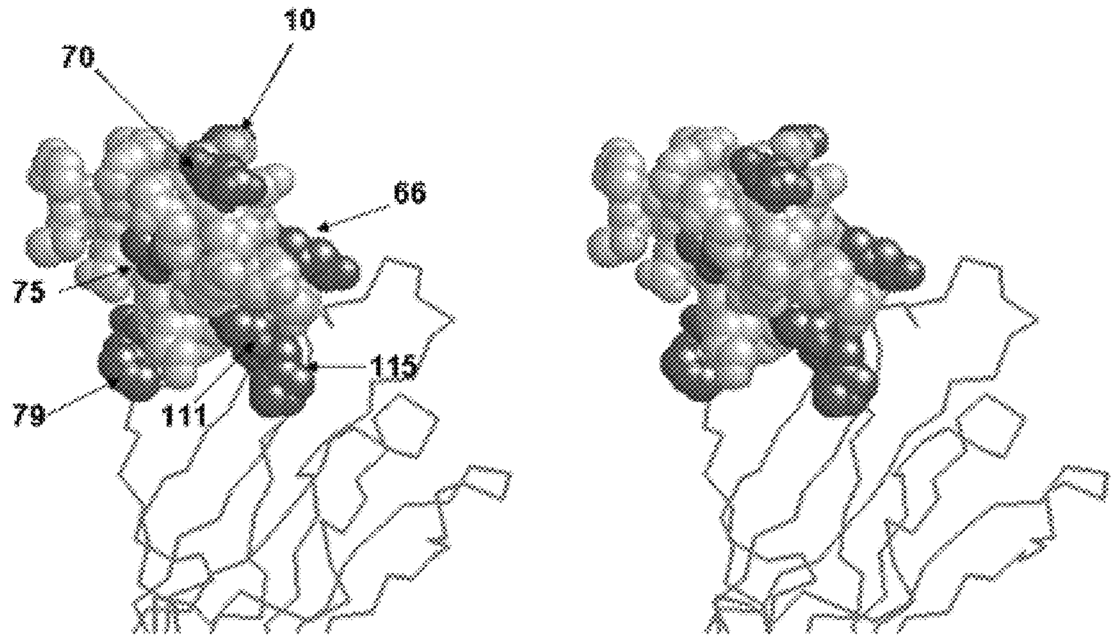

The *Torpedo* and mammalian MIR structures may be different enough to affect mAb recognition. An examination of the *Torpedo* MIR and mammalian MIR show some striking differences in the orientation and accessibility of critical MIR amino acids. The three MIR segments from the *Torpedo* alpha subunit are more loosely packed than those of from the mouse, and the *Torpedo* N-terminal helix protrudes more from the cluster than does the mouse N-terminal helix (FIG. 8). The core MIR segment was mapped to the AChR α(67-76) (5,13). This cluster of amino acids is both tightly packed and surface accessible in both the *Torpedo* and mouse structure. However, their structural arrangement in the MIR is quite different. The core MIR is essential for MIR-directed mAb recognition. The *Torpedo* core MIR is much more centrally located in the ECD while the mouse core MIR sits more at the top in the mouse ECD structure (FIG. 9). This difference in the core MIR may account for the lack of mAb 35 and 132A binding to the human 39MIR.

An evolutionarily conserved MIR correlates with the finding that mAb 198 was able to bind the *Torpedo* 39MIR and human 39MIR. The MIR peptide mimics refold into structures that present epitopes recognized by mAb 198 despite the amino acid differences. Unlike mAb 198, mAb 35 and mAb 132A did not bind to either the human or rat 39 MIR mimics. Both mAbs bind to mammalian synapses and cause a passive transfer of EAMG in naïve rats, so they bind to the mammalian MIR in the native, folded, assembled mammalian AChR (7, 17, 20). Instead of a completely different epitope, the mAbs may have different preferences for residues that differ between the *Torpedo* and human MIR. These can disrupt important contacts. There is also the possibility that the human MIR mimics adopt an alternative more compact structure that is more stable than the *Torpedo* MIR mimic and consequently do not present the sub-states that mAbs 35 and 132A recognize.

Both mAb 35 and mAb 132A bind to TAChR and bind to rat/mouse and human synapses, suggesting the presence of their epitopes at mammalian neuromuscular junctions as well as in the *Torpedo* electric organ (7). The fact that both mAbs bound to the *Torpedo* but not the human MIR mimics was surprising. There are likely small but important differences in the orientation of certain important residues and the loss of surface exposure of these residues may be important for one mAb and not another.

The eight amino acid difference between the *Torpedo* the human MIR was enough to render the mimics unrecognizable by mAbs 35 and 132A (FIG. 3). A small number of amino acids determine the mAb epitopes and changes in these critical amino acids can affect mAb binding. For example, K10, 175, and D111 appear to be critical for all of the mAbs tested, as their substitution to the homologous human amino acids caused significantly decreased binding of mAbs raised initially against electric organ AChR. Additionally, 175 and D111 mutations also resulted in the complete loss of binding to the mutated mimic by mAb 35.

The I75V and D111Q mutated peptides had the most dramatic overall effect on MIR-directed mAb binding. The human 39MIR was back mutated at each of the most detrimental point mutations. However, none of the single back mutations restored mAb 132A binding, while the K10N, V75I, and Q111D mutations restored mAb 35 binding. The single point mutations improved mAb 198 binding compared to the human 39MIR. While individually the mutations did not greatly restore mAb binding, pairwise mutations started to restore binding to mAb 35 and 132A. The K10N/V75I/Q111D mutant showed improved binding to mAb 35 and 198 compared to the *Torpedo* 39MIR. The K10N/D70A/V75I/Q111D mutant did not improve anti-MIR mAb binding compared to the *Torpedo* 39MIR. The alanine at position 70 reduces mAb binding. The positive charge from the aspartic acid appears to be important for mAb binding. While no single substitution restored mAb 132A binding, a combination of two or more substitutions was able to restore partial mAb binding. The effect of the V75I mutation on mAb binding was surprising. The mutation was a minor change, going from a hydrophobic amino acid to a slightly larger hydrophobic amino acid. The K10N and D70A substitutions both remove a charge from the human 39MIR.

TABLE 1

Summary of Western blot of FIG. 5. Numerical values represent fold-change in binding relative to Torpedo 39MIR.

| Mutant | mAb 35 | mAb 132A | mAb 198 | mAb 334 |
|---|---|---|---|---|
| Torpedo 39MIR | 1.00 | 1.00 | 1.00 | 1.00 |
| N10K | 0.29 | 0.03 | 0.82 | 0.59 |
| L12F | 1.42 | 1.10 | 0.90 | 0.88 |
| R66K | 0.62 | 1.55 | 1.03 | 2.75 |
| A70D | 0.93 | 0.20 | 1.08 | 1.04 |
| I75V | — | 0.06 | 0.16 | 0.03 |

TABLE 1-continued

Summary of Western blot of FIG. 5. Numerical values represent fold-change in binding relative to Torpedo 39MIR.

| Mutant | mAb 35 | mAb 132A | mAb 198 | mAb 334 |
|---|---|---|---|---|
| R79H | 1.91 | 1.65 | 0.97 | 2.40 |
| D111Q | — | 0.07 | 0.16 | 0.02 |
| K115H | — | 0.40 | 1.07 | 0.42 |

'—' denotes no binding.

TABLE 2

Summary of Western blot of FIG. 7. Numerical values represent fold-change in binding relative to Torpedo 39MIR.

| Mutant | mAb 35 | mAb 132A | mAb 198 |
|---|---|---|---|
| Torpedo 39MIR | 1.00 | 1.00 | 1.00 |
| Human 39MIR | — | — | 0.09 |
| K10N/D70A | 0.31 | 0.16 | 0.72 |
| K10N/V75I | 1.10 | 1.25 | 1.79 |
| K10N/Q111D | 2.31 | 1.07 | 1.19 |
| V75I/Q111D | 0.92 | 3.34 | 2.71 |
| K10N/V75I/Q111D | 2.97 | 2.46 | 2.52 |
| K10N/D70A/V75I/Q111D | 1.70 | 0.99 | 0.99 |

'—' denotes no binding.

TABLE 3

Summary of binding by single-substitution human 39MIR mutants. Numerical values represent fold-change in binding relative to Torpedo 39MIR

| Mutant | mAb 35 | mAb 132A | mAb 198 |
|---|---|---|---|
| Torpedo 39MIR | 1.00 | 1.00 | 1.00 |
| Human 39MIR | — | — | 0.02 |
| K10N | 0.01 | — | 0.23 |
| D70A | — | — | 0.02 |
| V75I | 0.03 | — | 0.65 |
| Q111D | 0.06 | — | 0.59 |

'—' denotes no binding.

References

1. Lindstrom, J. M., *Acetylcholine receptors and myasthenia*. Muscle Nerve, 2000. 23(4): p. 453-77.
2. Richman, D. P., et al., *Effector mechanisms of myasthenic antibodies*. Ann N Y Acad Sci, 1993. 681: p. 264-73.
3. Beroukhim, R. and N. Unwin, *Three-dimensional location of the main immunogenic region of the acetylcholine receptor*. Neuron, 1995. 15(2): p. 323-31.
4. Conti-Tronconi, B., S. Tzartos, and J. Lindstrom, *Monoclonal antibodies as probes of acetylcholine receptor structure. 2. Binding to native receptor*. Biochemistry, 1981. 20(8): p. 2181-91.
5. Papadouli, I., et al., *Antigenic role of single residues within the main immunogenic region of the nicotinic acetylcholine receptor*. Biochem J, 1990. 269(1): p. 239-45.
6. Tzartos, S. J., et al., *Main immunogenic region of Torpedo electroplax and human muscle acetylcholine receptor: localization and microheterogeneity revealed by the use of synthetic peptides*. J Neurochem, 1990. 54(1): p. 51-61.
7. Gomez, C. M., et al., *Monoclonal hybridoma anti-acetylcholine receptor antibodies: antibody specificity and effect of passive transfer*. Ann N Y Acad Sci, 1981. 377: p. 97-109.
8. Tzartos, S. J., M. E. Seybold, and J. M. Lindstrom, *Specificities of antibodies to acetylcholine receptors in*

*sera from myasthenia gravis patients measured by monoclonal antibodies*. Proc Natl Acad Sci USA, 1982. 79(1): p. 188-92.

9. Morell, S. W., et al., *Structural characterization of the main immunogenic region of the Torpedo acetylcholine receptor*. Mol Immunol, 2014. 58(1): p. 116-31.
10. Tzartos, S. J. and J. M. Lindstrom, *Monoclonal antibodies used to probe acetylcholine receptor structure: localization of the main immunogenic region and detection of similarities between subunits*. Proc Natl Acad Sci USA, 1980. 77(2): p. 755-9.
11. Tzartos, S. J., et al., *Mapping of surface structures of electrophorus acetylcholine receptor using monoclonal antibodies*. J Biol Chem, 1981. 256(16): p. 8635-45.
12. Unwin, N., *Refined structure of the nicotinic acetylcholine receptor at 4A resolution*. J Mol Biol, 2005. 346(4): p. 967-89.
13. Tzartos, S. J., et al., *Localization of the main immunogenic region of human muscle acetylcholine receptor to residues* 67-76 *of the alpha subunit*. Proc Natl Acad Sci USA, 1988. 85(9): p. 2899-903.
14. Trinh, V. B., A. J. Foster, and R. H. Fairclough, *Design, synthesis, and characterization of a* 39 *amino acid peptide mimic of the main immunogenic region of the Torpedo acetylcholine receptor*. Mol Immunol, 2014. 59(1): p. 79-90.
15. Trinh, V. B., *Therapeutic peptide mimics of the acetylcholine receptor main immunogenic region for treating myasthenia gravis*. 2013, (Doctoral dissertation). Retrieved from ProQuest Dissertations and Theses. (Accession Order No. 1449416596).
16. Boulter, J., et al., *Isolation of a clone coding for the alpha-subunit of a mouse acetylcholine receptor*. J Neurosci, 1985. 5(9): p. 2545-52.
17. Gomez, C. M. and D. P. Richman, *Monoclonal anti-acetylcholine receptor antibodies with differing capacities to induce experimental autoimmune myasthenia gravis*. J Immunol, 1985. 135(1): p. 234-41.
18. Richman, D. P., et al., *Monoclonal anti-acetylcholine receptor antibodies can cause experimental myasthenia*. Nature, 1980. 286(5774): p. 738-9.
19. Lindstrom, J. M., et al., *Pathological mechanisms in experimental autoimmune myasthenia gravis. II. Passive transfer of experimental autoimmune myasthenia gravis in rats with anti-acetylcholine receptor antibodies*. J Exp Med, 1976. 144(3): p. 739-53.
20. Tzartos, S., et al., *Passive transfer of experimental autoimmune myasthenia gravis by monoclonal antibodies to the main immunogenic region of the acetylcholine receptor*. J Neuroimmunol, 1987. 15(2): p. 185-94.
21. Fostieri, E., D. Beeson, and S. J. Tzartos, *The conformation of the main immunogenic region on the alpha-subunit of muscle acetylcholine receptor is affected by neighboring receptor subunits*. FEBS Lett, 2000. 481(2): p. 127-30.
22. Barchan, D., et al., *Modulation of the anti-acetylcholine receptor response and experimental autoimmune myasthenia gravis by recombinant fragments of the acetylcholine receptor*. Eur J Immunol, 1998. 28(2): p. 616-24.
23. Venkatesh, N., et al., *Prevention of passively transferred experimental autoimmune myasthenia gravis by a phage library-derived cyclic peptide*. Proc Natl Acad Sci USA, 2000. 97(2): p. 761-6.

Example 2. Fe-fusion Protein for the Treatment of Myasthenia Gravis

This example shows the design and creation of a fusion protein comprising peptides of the present invention and an antibody Fc domain that is suitable for the prevention or treatment of myasthenia gravis (MG).

Introduction

Seventy percent or more of the anti-acetylcholine receptor (AChR) antibodies (Abs) in the sera of MG patients are directed to the main immunogenic region (MIR) of the AChR. As shown in FIG. 12A, a peptide of the present invention has been designed (SEQ ID NO:27) that combines parts of the *Torpedo* and human MIR peptides (SEQ. ID NOS:8 and 9, respectively). This peptide binds anti-MIR monoclonal antibodies (mAbs) derived from rats and well as a fraction of Abs in MG patient sera.

Results

Figure 12B:
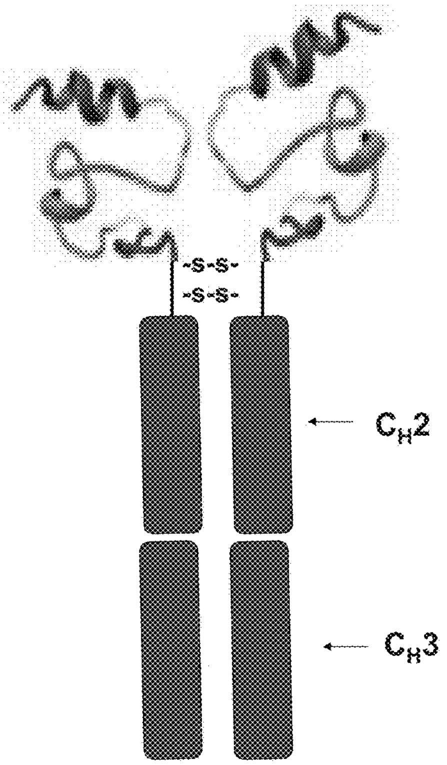
Figure 13:
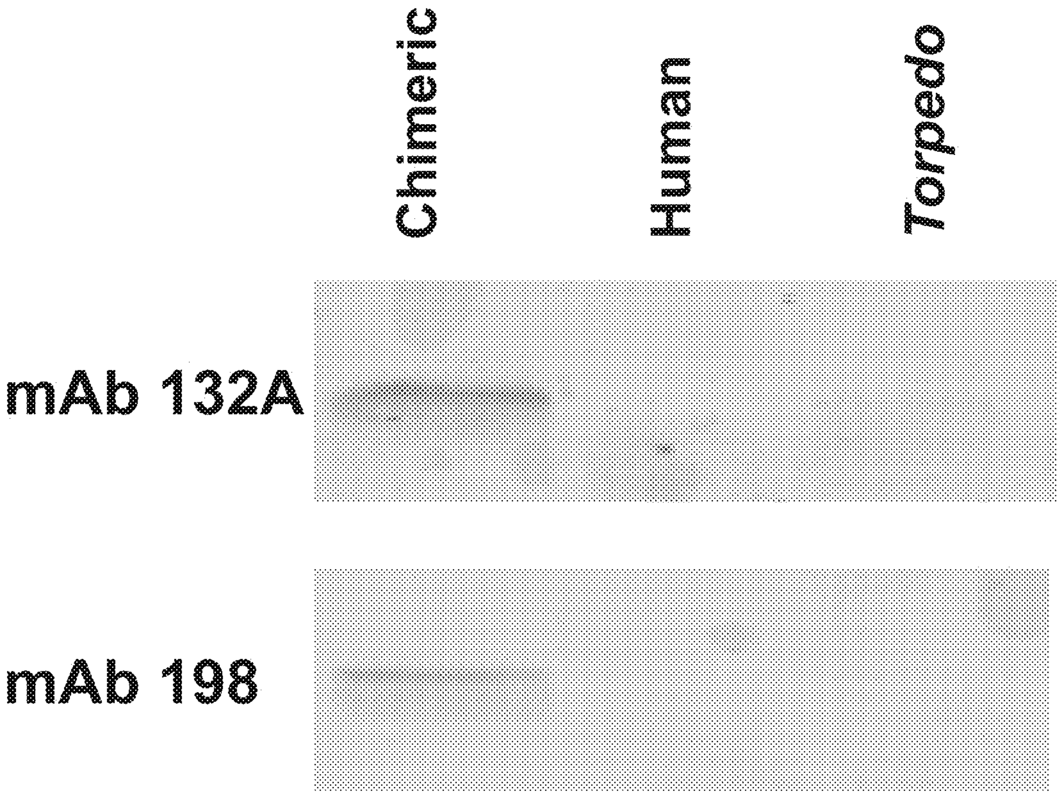
FIG. 13 shows a Western blot that illustrates binding of mAbs 132A and 198 to peptide-Fc conjugates (peptides of SEQ ID NOS:27 (chimeric), 8 (human) and 9 (*Torpedo*) conjugated to a human IgG antibody Fc domain plus hinge).

A conjugate has been engineered (FIG. 12B) that fuses the chimeric *Torpedo*-human peptide (SEQ ID NO:27) to an antibody Fc domain. The Western blot in FIG. 13 shows that while the *Torpedo* and human-based peptide-Fc conjugates (i.e., conjugates comprising the peptides of SEQ ID NOS; 8 and 9 fused to antibody Fc domains) did not bind the pathogenic mAbs 132A and 198, the chimeric peptide-Fc conjugate (i.e., a conjugate comprising the peptide of SEQ ID NO:27 fused to an antibody Fc domain) did recognize and bind both mAbs. This shows that the chimeric conjugate can bind and neutralize pathogenic Abs in MG patient sera.

Figure 14A:
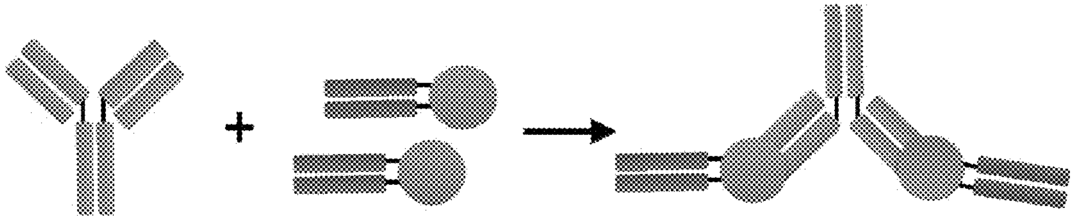
FIGS. 14A and 14B show different ways in which a peptide-Fc conjugate of the present invention can prevent or treat MG.
Figure 14B:
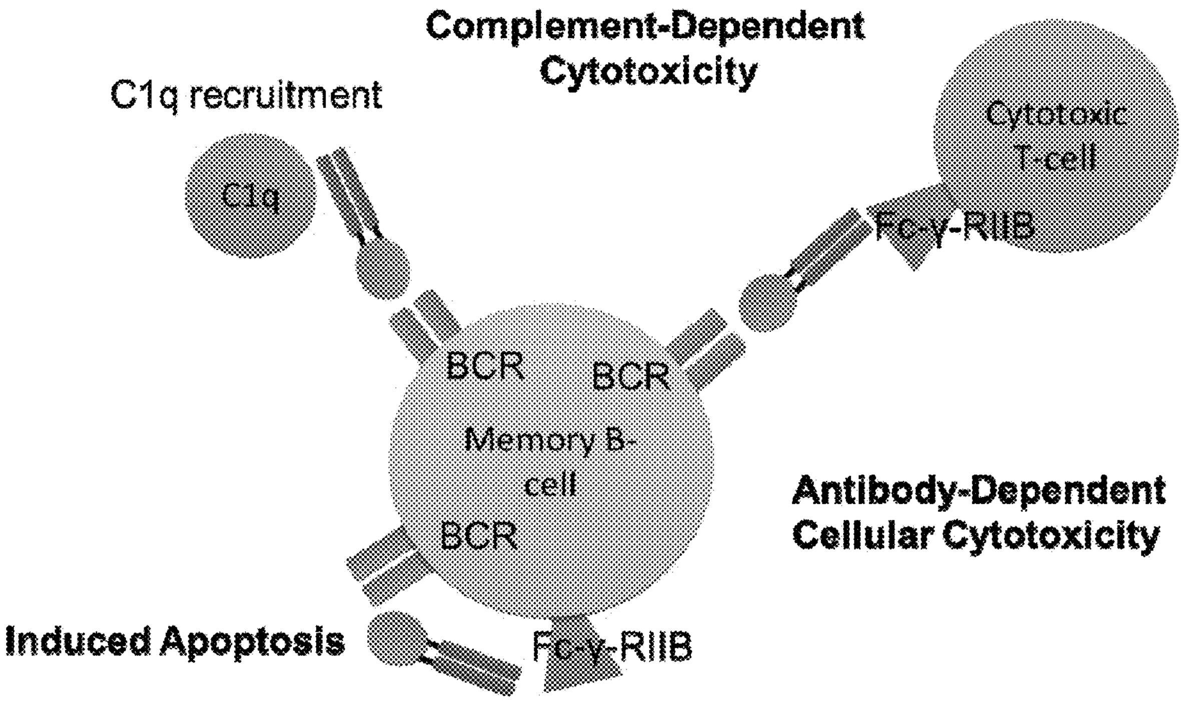

These results show that a peptide-Fc conjugate of the present invention (e.g., a peptide of SEQ ID NO:27 fused to an antibody Fc domain) is useful for preventing or treating MG. In addition to acting as a recognition domain that can bind to and block the combining sites of pathogenic anti-MIR Abs (FIG. 14A), the conjugate can also target the B-cell receptors on memory B-cells that are responsible for the production of the pathogenic anti-MIR Abs in MG (FIG. 14B). The construct can bind to those B-cells and induce the immune system destruction of them via complement activation, antibody-dependent cell-mediated cytotoxic killing, or crosslinking the B cell receptor to the FcγRIIb receptors, thus inducing apoptosis. Thus the conjugate is useful for inactivating, in an antigen-specific manner, only the pathogenic Ab response rather than depressing all adaptive immune responses.

V. Exemplary Embodiments

Exemplary embodiments provided in accordance with the presently disclosed subject matter include, but are not limited to, the claims and the following embodiments:

1. An isolated peptide comprising the amino acid sequence SEHETRLVA$X_1$LF$Z_1$LKWNP$X_2$DYGG$X_3$KKIH$Z_2$L$X_4$YTGH (SEQ ID NO:31) and amino acid modifications relative to the amino acid sequence set forth in SEQ ID NO:1 at two or more positions selected from the group consisting of $X_1$, $X_2$, $X_3$, and $X_4$, wherein $X_1$, $X_2$, $X_3$, and $X_4$ are independently selected amino acids and $Z_1$ and $Z_2$ are linker sequences of independent lengths comprising independently selected amino acids.
2. The peptide of embodiment 1, wherein the amino acid modifications are at $X_1$ and $X_2$ relative to the amino acid sequence set forth in SEQ ID NO:1.
3. The peptide of embodiment 2, wherein $X_1$ is N, $X_2$ is A, the length of $Z_1$ is 4, and the length of $Z_2$ is 2 (SEQ ID NO:2).
4. The peptide of embodiment 1, wherein the amino acid modifications are at $X_1$ and $X_3$ relative to the amino acid sequence set forth in SEQ ID NO:1.
5. The peptide of embodiment 4, wherein $X_1$ is N, $X_3$ is I, the length of $Z_1$ is 4, and the length of $Z_2$ is 2 (SEQ ID NO:3).

6. The peptide of embodiment 1, wherein the amino acid modifications are at $X_1$ and $X_4$ relative to the amino acid sequence set forth in SEQ ID NO:1.

7. The peptide of embodiment 6, wherein $X_1$ is N, $X_4$ is D, the length of $Z_1$ is 4, and the length of $Z_2$ is 2 (SEQ ID NO:4).

8. The peptide of embodiment 1, wherein the amino acid modifications are at $X_3$ and $X_4$ relative to the amino acid sequence set forth in SEQ ID NO:1.

9. The peptide of embodiment 8, wherein the amino acid sequence is not SEQ ID NO:5.

10. The peptide of embodiment 1, wherein the amino acid modifications are at $X_1$, $X_3$, and $X_4$ relative to the amino acid sequence set forth in SEQ ID NO:1.

11. The peptide of embodiment 10, wherein $X_1$ is N, $X_3$ is I, $X_4$ is D, the length of $Z_1$ is 4, and the length of $Z_2$ is 2 (SEQ ID NO:6).

12. The peptide of embodiment 1, wherein the amino acid modifications are at $X_1$, $X_2$, $X_3$, and $X_4$ relative to the amino acid sequence set forth in SEQ ID NO:1.

13. The peptide of embodiment 12, wherein $X_1$ is N, $X_2$ is A, $X_3$ is I, $X_4$ is D, the length of $Z_1$ is 4, and the length of $Z_2$ is 2 (SEQ ID NO:7).

14. The peptide of any one of embodiments 1 to 13, wherein the peptide binds to an antibody that binds to the main immunogenic region (MIR) of an acetylcholine receptor (AChR).

15. The peptide of any one of embodiments 1 to 14, further comprising an intein-chitin biding domain tag.

16. The peptide of any one of embodiments 1 to 15, further comprising a hexahistidine tag.

17. The peptide of any one of embodiments 1 to 16, further comprising an antibody heavy chain fragment that is conjugated to the peptide.

18. The peptide of embodiment 17, wherein the antibody is human immunoglobulin G.

19. The peptide of embodiment 17 or 18, wherein the hinge region of the heavy chain fragment is conjugated to the C-terminal end of the peptide.

20. A composition comprising a peptide of any one of embodiments 1 to 19 or a plurality thereof.

21. The composition of embodiment 20, further comprising a pharmaceutically acceptable carrier.

22. The composition of embodiment 20 or 21, wherein the plurality of peptides comprises at least 2, 3, 4, or 5 different peptides.

23. A kit comprising a peptide of any one of embodiments 1 to 19 or a plurality thereof and a solid support.

24. The kit of embodiment 23, wherein the solid support is a multiwell plate, an ELISA plate, a microarray, a chip, a bead, a porous strip, or a nitrocellulose filter.

25. The kit of embodiment 24, wherein the bead comprises chitin.

26. The kit of any one of embodiments 23 to 25, wherein the peptide or plurality thereof is immobilized on the solid support.

27. The kit of any one of embodiments 23 to 26, wherein the plurality of peptides binds to the same antibody or different antibodies that bind to the main immunogenic region (MIR) of an acetylcholine receptor (AChR).

28. The kit of any one of embodiments 23 to 27, further comprising instructions for use.

29. An isolated nucleic acid encoding an isolated peptide of any one of embodiments 1 to 19.

30. A method for detecting or determining the severity of myasthenia gravis (MG) in a subject, the method comprising:

detecting in a biological sample from the subject the presence or absence of antibodies that bind to a peptide of any one of embodiments 1 to 19 or a plurality thereof, wherein the presence of antibodies that bind to the peptide or plurality thereof indicates the presence or an increased severity of MG.

31. The method of embodiment 30, wherein the antibodies bind to the main immunogenic region (MIR) of an acetylcholine receptor (AChR).

32. The method of embodiment 30 or 31, wherein the peptide or plurality thereof is selected from the group consisting of SEQ ID NOS:2, 3, 4, 6, and 7.

33. The method of any one of embodiments 30 to 32, wherein the method further comprises obtaining the sample from the subject.

34. The method of any one of embodiments 30 to 33, wherein the sample is whole blood, serum, or plasma.

35. The method of any one of embodiments 30 to 34, wherein the peptide or plurality thereof is attached to a solid support.

36. The method of embodiment 35, wherein the solid support is a multiwell plate, an ELISA plate, a microarray, a chip, a bead, a porous strip, or a nitrocellulose filter.

37. The method of embodiment 36, wherein the bead comprises chitin.

38. The method of any one of embodiments 30 to 37, wherein the antibodies are detected by Western blot, dot blot, ELISA, radioimmunoassay, immunoprecipitation, electrochemiluminescence, immunofluorescence, FACS analysis, or multiplex bead assay.

39. The method of any one of embodiments 30 to 38, wherein the sample is compared to a control.

40. The method of embodiment 39, wherein the control is obtained from a subject who does not have MG.

41. The method of embodiment 39, wherein the control is obtained from the subject before developing symptoms of MG or after receiving treatment for MG.

42. A method for preventing or treating myasthenia gravis (MG) in a subject, the method comprising:

administering to the subject a therapeutically effective amount of a peptide of any one of embodiments 1 to 19 or a plurality thereof, wherein the peptide or plurality thereof binds to antibodies circulating in the subject to form neutralizing complexes, thereby preventing or treating MG.

43. The method of embodiment 42, wherein the circulating antibodies bind to the main immunogenic region (MIR) of an acetylcholine receptor (AChR).

44. The method of embodiment 42 or 43, wherein the peptide or plurality thereof is selected from the group consisting of SEQ ID NOS:2, 3, 4, 6, and 7.

45. The method of any one of embodiments 42 to 44, wherein the peptide or plurality thereof inactivates or reduces the number of memory B-cells that produce antibodies that bind to the MIR of an AChR.

46. The method of any one of embodiments 42 to 45, wherein the subject is exhibiting symptoms of MG.

47. The method of embodiment 46, wherein treating the subject results in a decrease in the symptoms of MG.

48. The method of any one of embodiments 42 to 47, further comprising removing the neutralizing complexes from the subject.

49. The method of embodiment 48, wherein the neutralizing complexes are removed by affinity plasmapheresis.

50. The method of any one of embodiments 42 to 49, wherein the peptide or plurality thereof is administered intravenously, intramuscularly, or a combination thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence reference numbers cited herein are hereby incorporated by reference in their entirety for all purposes.

Informal Sequence Listing

TABLE 4

Peptide sequences.

| SEQ ID NO: | Sequence | Notes |
|---|---|---|
| 1 | SEHETRLVAKLF$Z_1$LKWNPDDYGGVKKIH$Z_2$LQYTGH | Human MIR (variable linkers) |
| 2 | SEHETRLVANLF$Z_1$LKWNPADYGGVKKIH$Z_2$LQYTGH | Human MIR double mutant (K10N/D70A)(variable linkers) |
| 3 | SEHETRLVANLF$Z_1$LKWNPDDYGGIKKIH$Z_2$LQYTGH | Human MIR double mutant (K10N/V75I)(variable linkers) |
| 4 | SEHETRLVANLF$Z_1$LKWNPDDYGGVKKIH$Z_2$LDYTGH | Human MIR double mutant (K10N/Q111D)(variable linkers) |
| 5 | SEHETRLVAKLFGGGSLKWNPDDYGGIKKIHGSLDYTGH | Human MIR double mutant (V75I/Q111D) |
| 6 | SEHETRLVANLF$Z_1$LKWNPDDYGGIKKIH$Z_2$LDYTGH | Human MIR triple mutant (K10N/V75I/Q111D)(variable linkers) |
| 7 | SEHETRLVANLF$Z_1$LKWNPADYGGIKKIH$Z_2$LDYTGH | Human MIR quadruple mutant (K10N/D70A/V75I/Q111D) (variable linkers) |
| 8 | SEHETRLVAKLFGGGSLKWNPDDYGGVKKIHGSLQYTGH | Human 39MIR |
| 9 | SEHETRLVANLLGGGSLRWNPADYGGIKKIRGSLDYTGK | Torpedo 39MIR |
| 10 | SEHETRLVAKLFGGGSLKWNPDDYGGVKKIHGSLDYTGH | Mouse 39MIR |
| 11 | SEHETRLVAKLLGGGSLRWNPADYGGIKKIRGSLDYTGK | Torpedo 39MIR single mutant (N10K) |
| 12 | SEHETRLVANLFGGGSLRWNPADYGGIKKIRGSLDYTGK | Torpedo 39MIR single mutant (L12F) |
| 13 | SEHETRLVANLLGGGSLKWNPADYGGIKKIRGSLDYTGK | Torpedo 39MIR single mutant (R66K) |
| 14 | SEHETRLVANLLGGGSLRWNPDDYGGIKKIRGSLDYTGK | Torpedo 39MIR single mutant (A70D) |
| 15 | SEHETRLVANLLGGGSLRWNPADYGGVKKIRGSLDYTGK | Torpedo 39MIR single mutant (I75V) |
| 16 | SEHETRLVANLLGGGSLRWNPADYGGIKKIHGSLDYTGK | Torpedo 39MIR single mutant (R79H) |
| 17 | SEHETRLVANLLGGGSLRWNPADYGGIKKIRGSLQYTGK | Torpedo 39MIR single mutant (D111Q) |
| 18 | SEHETRLVANLLGGGSLRWNPADYGGIKKIRGSLDYTGH | Torpedo 39MIR single mutant (K115H) |
| 19 | SEHETRLVANLFGGGSLKWNPDDYGGVKKIHGSLQYTGH | Human 39MIR single mutant (K10N) |
| 20 | SEHETRLVAKLFGGGSLKWNPADYGGVKKIHGSLQYTGH | Human 39MIR single mutant (D70A) |
| 21 | SEHETRLVAKLFGGGSLKWNPDDYGGIKKIHGSLQYTGH | Human 39MIR single mutant (V75I) |
| 22 | SEHETRLVAKLFGGGSLKWNPDDYGGVKKIHGSLDYTGH | Human 39MIR single mutant (Q111D) |

TABLE 4-continued

| SEQ ID NO: | Sequence | Notes |
|---|---|---|
| | Peptide sequences. | |
| 23 | SEHETRLVANLFGGGSLKWNPADYGGVKKIHGSLQYTGH | Human 39MIR double mutant (K10N/D70A) |
| 24 | SEHETRLVANLFGGGSLKWNPDDYGGIKKIHGSLQYTGH | Human 39MIR double mutant (K10N/V75I) |
| 25 | SEHETRLVANLFGGGSLKWNPDDYGGVKKIHGSLDYTGH | Human 39MIR double mutant (K10N/Q111D) |
| 26 | SEHETRLVANLFGGGSLKWNPDDYGGIKKIHGSLDYTGH | Human 39MIR triple mutant (K10N/V75I/Q111D) |
| 27 | SEHETRLVANLFGGGSLKWNPADYGGIKKIHGSLDYTGH | Human 39MIR quadruple mutant (K10N/D70A/V75I/Q111D) |
| 28 | SEHETRLVANLLENYNKVIRPVEHHTHFVDITVGLQLIQLI SVDEVNQIVETNVRLRQQWIDVRLRWNPADYGGIKKIRLP SDDVWLPDLVLYNNADGDFAIVHMTKLLLDYTGKIMWT PPAIFKSYCEIIVTHFPFDQQNCTMKLGIWTYDGTKVSISPE | Torpedo nicotinic AChR alpha subunit, amino acids 1-161 of the extracellular domain |
| 29 | SEHETRLVANLLGGGSLRWNPADYGGIKKIHGSLDYTGH | Human 39MIR sextuple mutant (K10N/F12L/K66R/D70A/V75I/ Q111D) |
| 30 | SEHETRLVAKLFGGGSLKWNPDDYGGVKKIHGSLQYTGH | Human MIR ($Z_1$ linker is GGGS and $Z_2$ linker is GS; both underlined) |
| 31 | SEHETRLVA$X_1$LF$Z_1$LKWNP$X_2$DYGG$X_3$KKIH$Z_2$L$X_4$YTGH | Isolated peptide sequence |

What is claimed is:

1. An isolated peptide comprising the amino acid sequence $SEHETRLVAX_1LFZ_1LKWNPX_2DYGGX_3KKIHZ_2LX_4YTGH$ (SEQ ID NO:31), wherein:

(a) $X_1$ is N, $X_2$ is D, $X_3$ is I, $X_4$ is D, the length of $Z_1$ is 4, and the length of $Z_2$ is 2; or (b) $X_1$ is N, $X_2$ is A, $X_3$ is I, $X_4$ is D, the length of $Z_1$ is 4, and the length of $Z_2$ is 2, and $Z_1$ and $Z_2$ are linker sequences comprising independently selected amino acids.

2. The peptide of claim 1, wherein the peptide comprises the sequence of SEQ ID NO:26 or SEQ ID NO:27.

3. The peptide of claim 1, wherein the peptide binds to an antibody that binds to the main immunogenic region (MIR) of an acetylcholine receptor (AChR).

4. The peptide of claim 1, further comprising an antibody heavy chain fragment that is conjugated to the peptide.

5. The peptide of claim 4, wherein the antibody heavy chain fragment is derived from human immunoglobulin G, immunoglobulin A, immunoglobulin D, immunoglobulin E, immunoglobulin M, or a combination thereof.

6. The peptide of claim 4, wherein the hinge region of the antibody heavy chain fragment is conjugated to the C-terminal end of the peptide.

7. A method for treating myasthenia gravis (MG) in a subject, the method comprising:

administering to the subject a therapeutically effective amount of the peptide of claim 4 or a plurality thereof, wherein the peptide or plurality thereof binds to antibodies circulating in the subject to form neutralizing complexes, thereby treating MG.

8. The method of claim 7, wherin the circulating antibodies bind to the main immunogenic region (MIR) of an acetylcholine receptor (AChR).

9. The method of claim 7, wherein the peptide or plurality thereof inactivates or reduces the number of memory B-cells that produce antibodies that bind to the MIR of an AChR.

10. The method of claim 7, wherein the antibody heavy chain fragment is derived from human immunoglobulin G, immunoglobulin A, immunoglobulin D, immunoglobulin E, immunoglobulin M, or a combination thereof.

11. The method of claim 7, wherein the hinge region of the antibody heavy chain fragment is conjugated to the C-terminal end of the peptide.

12. The method of claim 7, wherein the antibody heavy chain fragment comprises an Fc domain.

13. The peptide of claim 4, wherein the antibody heavy chain fragment comprises an Fc domain.

14. A composition comprising the peptide of claim 1 or a plurality thereof.

15. A kit comprising the peptide of claim 1 or a plurality thereof and a solid support.

16. An isolated nucleic acid encoding the isolated peptide of claim 1.

17. A method for detecting in a biological sample from a subject the presence or absence of antibodies that bind to the peptide of claim 1 or a plurality thereof, the method comprising:

(a) contacting the biological sample with the peptide or plurality thereof, and (b) detecting the presence or absence of bound antibodies using western blot, dot blot, ELBA, radioimmunoassay, immunoprecipitation, electrochemiluminescence, immunofluorescence, FACS analysis, multiplex bead assay, or a combination thereof.

18. The method of claim 17, wherein the antibodies bind to the main immunogenic region (MIR) of an acetylcholine receptor (AChR).

19. A fusion protein comprising:

(i) a peptide comprising the amino acid sequence SEHETRLVA$X_1$LF$Z_1$LKWNP$X_2$DYGG$X_3$KKIH$Z_2$L$X_4$YTGH (SEQ ID NO:31), wherein:

(a) $X_1$ is N, $X_2$ is D, $X_3$ is I, $X_4$ is D, the length of $Z_1$ is 4, and the length of $Z_2$ is 2; or (b) $X_1$ is N, $X_2$ is A, $X_3$ is I, $X_4$ is D, the length of $Z_1$ is 4, and the length of $Z_2$ is 2, and $Z_1$ and $Z_2$ are linker sequences comprising independently selected amino acids; and (ii) an antibody heavy chain fragment, wherein the fragment comprises an Fc domain.

20. The fusion protein of claim 19, wherein the peptide comprises the sequence of SEQ ID NO:26 or SEQ ID NO:27.

21. The fusion protein of claim 19, wherein the antibody heavy chain fragment is derived from human immunoglobulin G, immunoglobulin A, immunoglobulin D, immunoglobulin E, immunoglobulin M, or a combination thereof.

22. The fusion protein of claim 19, wherein the antibody heavy chain fragment is conjugated to the C-terminal end of the peptide.

* * * * *

SEQUENCE LISTING

<160> NUMBER OF SEQ ID NOS: 32

<210> SEQ ID NO 1
<211> LENGTH: 233
<212> TYPE: PRT
<213> ORGANISM: Artificial Sequence
<220> FEATURE:
<223> OTHER INFORMATION: synthetic main immunogenic region (MIR) peptide
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(112)
<223> OTHER INFORMATION: Xaa is any amino acid; Xaa may be present or absent
<220> FEATURE:
<221> NAME/KEY: MISC_FEATURE
<222> LOCATION: (128)..(128)
<223> OTHER INFORMATION: Xaa is any amino acid
<220> FEATURE:
<221> NAME/KEY: MISC_FEATURE
<222> LOCATION: (129)..(227)
<223> OTHER INFORMATION: Xaa is any amino acid; Xaa may be present or absent

<400> SEQUENCE: 1

```
Ser Glu His Glu Thr Arg Leu Val Ala Lys Leu Phe Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30
```

```
Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Leu Lys Trp Asn Pro Asp Asp Tyr Gly Gly Val Lys Lys Ile His Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Leu Gln Tyr Thr Gly His
225                 230
```

<210> SEQ ID NO 2
<211> LENGTH: 233
<212> TYPE: PRT
<213> ORGANISM: Artificial Sequence
<220> FEATURE:
<223> OTHER INFORMATION: synthetic main immunogenic region (MIR) peptide
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(112)
<223> OTHER INFORMATION: Xaa is any amino acid; Xaa may be present or absent
<220> FEATURE:
<221> NAME/KEY: MISC_FEATURE
<222> LOCATION: (128)..(128)
<223> OTHER INFORMATION: Xaa is any amino acid
<220> FEATURE:
<221> NAME/KEY: MISC_FEATURE
<222> LOCATION: (129)..(227)
<223> OTHER INFORMATION: Xaa is any amino acid; Xaa may be present or absent

<400> SEQUENCE: 2

```
Ser Glu His Glu Thr Arg Leu Val Ala Asn Leu Phe Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60
```

-continued

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Leu Lys Trp Asn Pro Ala Asp Tyr Gly Gly Val Lys Lys Ile His Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Leu Gln Tyr Thr Gly His
225                 230


<210> SEQ ID NO 3
<211> LENGTH: 233
<212> TYPE: PRT
<213> ORGANISM: Artificial Sequence
<220> FEATURE:
<223> OTHER INFORMATION: synthetic main immunogenic region (MIR) peptide
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(112)
<223> OTHER INFORMATION: Xaa is any amino acid; Xaa may be present or
      absent
<220> FEATURE:
<221> NAME/KEY: MISC_FEATURE
<222> LOCATION: (128)..(128)
<223> OTHER INFORMATION: Xaa is any amino acid
<220> FEATURE:
<221> NAME/KEY: MISC_FEATURE
<222> LOCATION: (129)..(227)
<223> OTHER INFORMATION: Xaa is any amino acid; Xaa may be present or
      absent

<400> SEQUENCE: 3

Ser Glu His Glu Thr Arg Leu Val Ala Asn Leu Phe Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95
```

-continued

```
Xaa Xaa Xaa Xaa Xaa Xaa Xaa Xaa Xaa Xaa Xaa Xaa Xaa Xaa Xaa Xaa
            100                 105                 110

Leu Lys Trp Asn Pro Asp Asp Tyr Gly Gly Ile Lys Lys Ile His Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Leu Gln Tyr Thr Gly His
225                 230


<210> SEQ ID NO 4
<211> LENGTH: 233
<212> TYPE: PRT
<213> ORGANISM: Artificial Sequence
<220> FEATURE:
<223> OTHER INFORMATION: synthetic main immunogenic region (MIR) peptide
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(112)
<223> OTHER INFORMATION: Xaa is any amino acid; Xaa may be present or
      absent
<220> FEATURE:
<221> NAME/KEY: MISC_FEATURE
<222> LOCATION: (128)..(128)
<223> OTHER INFORMATION: Xaa is any amino acid
<220> FEATURE:
<221> NAME/KEY: MISC_FEATURE
<222> LOCATION: (129)..(227)
<223> OTHER INFORMATION: Xaa is any amino acid; Xaa may be present or
      absent

<400> SEQUENCE: 4

Ser Glu His Glu Thr Arg Leu Val Ala Asn Leu Phe Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Leu Lys Trp Asn Pro Asp Asp Tyr Gly Gly Val Lys Lys Ile His Xaa
        115                 120                 125
```

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Leu Asp Tyr Thr Gly His
225                 230

<210> SEQ ID NO 5
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 5

Ser Glu His Glu Thr Arg Leu Val Ala Lys Leu Phe Gly Gly Gly Ser
1               5                   10                  15

Leu Lys Trp Asn Pro Asp Asp Tyr Gly Gly Ile Lys Lys Ile His Gly
            20                  25                  30

Ser Leu Asp Tyr Thr Gly His
        35

<210> SEQ ID NO 6
<211> LENGTH: 233
<212> TYPE: PRT
<213> ORGANISM: Artificial Sequence
<220> FEATURE:
<223> OTHER INFORMATION: synthetic main immunogenic region (MIR) peptide
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(112)
<223> OTHER INFORMATION: Xaa is any amino acid; Xaa may be present or absent
<220> FEATURE:
<221> NAME/KEY: MISC_FEATURE
<222> LOCATION: (128)..(128)
<223> OTHER INFORMATION: Xaa is any amino acid
<220> FEATURE:
<221> NAME/KEY: MISC_FEATURE
<222> LOCATION: (129)..(227)
<223> OTHER INFORMATION: Xaa is any amino acid; Xaa may be present or absent

<400> SEQUENCE: 6

Ser Glu His Glu Thr Arg Leu Val Ala Asn Leu Phe Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Leu Lys Trp Asn Pro Asp Asp Tyr Gly Gly Ile Lys Lys Ile His Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Leu Asp Tyr Thr Gly His
225                 230


<210> SEQ ID NO 7
<211> LENGTH: 233
<212> TYPE: PRT
<213> ORGANISM: Artificial Sequence
<220> FEATURE:
<223> OTHER INFORMATION: synthetic main immunogenic region (MIR) peptide
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(112)
<223> OTHER INFORMATION: Xaa is any amino acid; Xaa may be present or
      absent
<220> FEATURE:
<221> NAME/KEY: MISC_FEATURE
<222> LOCATION: (128)..(128)
<223> OTHER INFORMATION: Xaa is any amino acid
<220> FEATURE:
<221> NAME/KEY: MISC_FEATURE
<222> LOCATION: (129)..(227)
<223> OTHER INFORMATION: Xaa is any amino acid; Xaa may be present or
      absent

<400> SEQUENCE: 7

Ser Glu His Glu Thr Arg Leu Val Ala Asn Leu Phe Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95
```

Xaa Xaa Xaa Xaa Xaa Xaa Xaa Xaa Xaa Xaa Xaa Xaa Xaa Xaa Xaa Xaa
100 105 110

Leu Lys Trp Asn Pro Ala Asp Tyr Gly Gly Ile Lys Lys Ile His Xaa
115 120 125

Xaa Xaa Xaa Xaa Xaa Xaa Xaa Xaa Xaa Xaa Xaa Xaa Xaa Xaa Xaa Xaa
130 135 140

Xaa Xaa Xaa Xaa Xaa Xaa Xaa Xaa Xaa Xaa Xaa Xaa Xaa Xaa Xaa Xaa
145 150 155 160

Xaa Xaa Xaa Xaa Xaa Xaa Xaa Xaa Xaa Xaa Xaa Xaa Xaa Xaa Xaa Xaa
165 170 175

Xaa Xaa Xaa Xaa Xaa Xaa Xaa Xaa Xaa Xaa Xaa Xaa Xaa Xaa Xaa Xaa
180 185 190

Xaa Xaa Xaa Xaa Xaa Xaa Xaa Xaa Xaa Xaa Xaa Xaa Xaa Xaa Xaa Xaa
195 200 205

Xaa Xaa Xaa Xaa Xaa Xaa Xaa Xaa Xaa Xaa Xaa Xaa Xaa Xaa Xaa Xaa
210 215 220

Xaa Xaa Xaa Leu Asp Tyr Thr Gly His
225 230

<210> SEQ ID NO 8
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 8

Ser Glu His Glu Thr Arg Leu Val Ala Lys Leu Phe Gly Gly Gly Ser
1 5 10 15

Leu Lys Trp Asn Pro Asp Asp Tyr Gly Gly Val Lys Lys Ile His Gly
20 25 30

Ser Leu Gln Tyr Thr Gly His
35

<210> SEQ ID NO 9
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 9

Ser Glu His Glu Thr Arg Leu Val Ala Asn Leu Leu Gly Gly Gly Ser
1 5 10 15

Leu Arg Trp Asn Pro Ala Asp Tyr Gly Gly Ile Lys Lys Ile Arg Gly
20 25 30

Ser Leu Asp Tyr Thr Gly Lys
35

<210> SEQ ID NO 10
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 10

Ser Glu His Glu Thr Arg Leu Val Ala Lys Leu Phe Gly Gly Gly Ser
1 5 10 15

```
Leu Lys Trp Asn Pro Asp Asp Tyr Gly Gly Val Lys Lys Ile His Gly
            20                  25                  30

Ser Leu Asp Tyr Thr Gly His
        35


<210> SEQ ID NO 11
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 11

Ser Glu His Glu Thr Arg Leu Val Ala Lys Leu Leu Gly Gly Gly Ser
1               5                   10                  15

Leu Arg Trp Asn Pro Ala Asp Tyr Gly Gly Ile Lys Lys Ile Arg Gly
            20                  25                  30

Ser Leu Asp Tyr Thr Gly Lys
        35


<210> SEQ ID NO 12
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 12

Ser Glu His Glu Thr Arg Leu Val Ala Asn Leu Phe Gly Gly Gly Ser
1               5                   10                  15

Leu Arg Trp Asn Pro Ala Asp Tyr Gly Gly Ile Lys Lys Ile Arg Gly
            20                  25                  30

Ser Leu Asp Tyr Thr Gly Lys
        35


<210> SEQ ID NO 13
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 13

Ser Glu His Glu Thr Arg Leu Val Ala Asn Leu Leu Gly Gly Gly Ser
1               5                   10                  15

Leu Lys Trp Asn Pro Ala Asp Tyr Gly Gly Ile Lys Lys Ile Arg Gly
            20                  25                  30

Ser Leu Asp Tyr Thr Gly Lys
        35


<210> SEQ ID NO 14
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 14

Ser Glu His Glu Thr Arg Leu Val Ala Asn Leu Leu Gly Gly Gly Ser
1               5                   10                  15

Leu Arg Trp Asn Pro Asp Asp Tyr Gly Gly Ile Lys Lys Ile Arg Gly
            20                  25                  30
```

Ser Leu Asp Tyr Thr Gly Lys
35

<210> SEQ ID NO 15
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 15

Ser Glu His Glu Thr Arg Leu Val Ala Asn Leu Leu Gly Gly Gly Ser
1 5 10 15

Leu Arg Trp Asn Pro Ala Asp Tyr Gly Gly Val Lys Lys Ile Arg Gly
20 25 30

Ser Leu Asp Tyr Thr Gly Lys
35

<210> SEQ ID NO 16
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 16

Ser Glu His Glu Thr Arg Leu Val Ala Asn Leu Leu Gly Gly Gly Ser
1 5 10 15

Leu Arg Trp Asn Pro Ala Asp Tyr Gly Gly Ile Lys Lys Ile His Gly
20 25 30

Ser Leu Asp Tyr Thr Gly Lys
35

<210> SEQ ID NO 17
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 17

Ser Glu His Glu Thr Arg Leu Val Ala Asn Leu Leu Gly Gly Gly Ser
1 5 10 15

Leu Arg Trp Asn Pro Ala Asp Tyr Gly Gly Ile Lys Lys Ile Arg Gly
20 25 30

Ser Leu Gln Tyr Thr Gly Lys
35

<210> SEQ ID NO 18
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 18

Ser Glu His Glu Thr Arg Leu Val Ala Asn Leu Leu Gly Gly Gly Ser
1 5 10 15

Leu Arg Trp Asn Pro Ala Asp Tyr Gly Gly Ile Lys Lys Ile Arg Gly
20 25 30

Ser Leu Asp Tyr Thr Gly His
35

-continued

<210> SEQ ID NO 19
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 19

```
Ser Glu His Glu Thr Arg Leu Val Ala Asn Leu Phe Gly Gly Gly Ser
1               5                   10                  15

Leu Lys Trp Asn Pro Asp Asp Tyr Gly Gly Val Lys Lys Ile His Gly
            20                  25                  30

Ser Leu Gln Tyr Thr Gly His
        35
```

<210> SEQ ID NO 20
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 20

```
Ser Glu His Glu Thr Arg Leu Val Ala Lys Leu Phe Gly Gly Gly Ser
1               5                   10                  15

Leu Lys Trp Asn Pro Ala Asp Tyr Gly Gly Val Lys Lys Ile His Gly
            20                  25                  30

Ser Leu Gln Tyr Thr Gly His
        35
```

<210> SEQ ID NO 21
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 21

```
Ser Glu His Glu Thr Arg Leu Val Ala Lys Leu Phe Gly Gly Gly Ser
1               5                   10                  15

Leu Lys Trp Asn Pro Asp Asp Tyr Gly Gly Ile Lys Lys Ile His Gly
            20                  25                  30

Ser Leu Gln Tyr Thr Gly His
        35
```

<210> SEQ ID NO 22
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 22

```
Ser Glu His Glu Thr Arg Leu Val Ala Lys Leu Phe Gly Gly Gly Ser
1               5                   10                  15

Leu Lys Trp Asn Pro Asp Asp Tyr Gly Gly Val Lys Lys Ile His Gly
            20                  25                  30

Ser Leu Asp Tyr Thr Gly His
        35
```

<210> SEQ ID NO 23
<211> LENGTH: 39

<212> TYPE: PRT
<213> ORGANISM: Artificial Sequence
<220> FEATURE:
<223> OTHER INFORMATION: synthetic main immunogenic region (MIR) peptide

<400> SEQUENCE: 23

```
Ser Glu His Glu Thr Arg Leu Val Ala Asn Leu Phe Gly Gly Gly Ser
1               5                   10                  15

Leu Lys Trp Asn Pro Ala Asp Tyr Gly Gly Val Lys Lys Ile His Gly
            20                  25                  30

Ser Leu Gln Tyr Thr Gly His
        35
```

<210> SEQ ID NO 24
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 24

```
Ser Glu His Glu Thr Arg Leu Val Ala Asn Leu Phe Gly Gly Gly Ser
1               5                   10                  15

Leu Lys Trp Asn Pro Asp Asp Tyr Gly Gly Ile Lys Lys Ile His Gly
            20                  25                  30

Ser Leu Gln Tyr Thr Gly His
        35
```

<210> SEQ ID NO 25
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 25

```
Ser Glu His Glu Thr Arg Leu Val Ala Asn Leu Phe Gly Gly Gly Ser
1               5                   10                  15

Leu Lys Trp Asn Pro Asp Asp Tyr Gly Gly Val Lys Lys Ile His Gly
            20                  25                  30

Ser Leu Asp Tyr Thr Gly His
        35
```

<210> SEQ ID NO 26
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 26

```
Ser Glu His Glu Thr Arg Leu Val Ala Asn Leu Phe Gly Gly Gly Ser
1               5                   10                  15

Leu Lys Trp Asn Pro Asp Asp Tyr Gly Gly Ile Lys Lys Ile His Gly
            20                  25                  30

Ser Leu Asp Tyr Thr Gly His
        35
```

<210> SEQ ID NO 27
<211> LENGTH: 39
<212> TYPE: PRT
<213> ORGANISM: Artificial Sequence
<220> FEATURE:

<223> OTHER INFORMATION: synthetic main immunogenic region (MIR) peptide

<400> SEQUENCE: 27

```
Ser Glu His Glu Thr Arg Leu Val Ala Asn Leu Phe Gly Gly Gly Ser
1               5                   10                  15

Leu Lys Trp Asn Pro Ala Asp Tyr Gly Gly Ile Lys Lys Ile His Gly
            20                  25                  30

Ser Leu Asp Tyr Thr Gly His
        35
```

<210> SEQ ID NO 28
<211> LENGTH: 161
<212> TYPE: PRT
<213> ORGANISM: Unknown
<220> FEATURE:
<223> OTHER INFORMATION: Torpedo sp.

<400> SEQUENCE: 28

```
Ser Glu His Glu Thr Arg Leu Val Ala Asn Leu Leu Glu Asn Tyr Asn
1               5                   10                  15

Lys Val Ile Arg Pro Val Glu His His Thr His Phe Val Asp Ile Thr
            20                  25                  30

Val Gly Leu Gln Leu Ile Gln Leu Ile Ser Val Asp Glu Val Asn Gln
        35                  40                  45

Ile Val Glu Thr Asn Val Arg Leu Arg Gln Gln Trp Ile Asp Val Arg
    50                  55                  60

Leu Arg Trp Asn Pro Ala Asp Tyr Gly Gly Ile Lys Lys Ile Arg Leu
65                  70                  75                  80

Pro Ser Asp Asp Val Trp Leu Pro Asp Leu Val Leu Tyr Asn Asn Ala
                85                  90                  95

Asp Gly Asp Phe Ala Ile Val His Met Thr Lys Leu Leu Leu Asp Tyr
            100                 105                 110

Thr Gly Lys Ile Met Trp Thr Pro Pro Ala Ile Phe Lys Ser Tyr Cys
        115                 120                 125

Glu Ile Ile Val Thr His Phe Pro Phe Asp Gln Gln Asn Cys Thr Met
    130                 135                 140

Lys Leu Gly Ile Trp Thr Tyr Asp Gly Thr Lys Val Ser Ile Ser Pro
145                 150                 155                 160

Glu
```

<210> SEQ ID NO 29
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 29

```
Ser Glu His Glu Thr Arg Leu Val Ala Asn Leu Leu Gly Gly Gly Ser
1               5                   10                  15

Leu Arg Trp Asn Pro Ala Asp Tyr Gly Gly Ile Lys Lys Ile His Gly
            20                  25                  30

Ser Leu Asp Tyr Thr Gly His
        35
```

<210> SEQ ID NO 30
<211> LENGTH: 39
<212> TYPE: PRT
<213> ORGANISM: Artificial Sequence
<220> FEATURE:
<223> OTHER INFORMATION: synthetic main immunogenic region (MIR) peptide

<400> SEQUENCE: 30

Ser Glu His Glu Thr Arg Leu Val Ala Lys Leu Phe Gly Gly Gly Ser
1 5 10 15

Leu Lys Trp Asn Pro Asp Asp Tyr Gly Gly Val Lys Lys Ile His Gly
20 25 30

Ser Leu Gln Tyr Thr Gly His
35

<210> SEQ ID NO 31
<211> LENGTH: 233
<212> TYPE: PRT
<213> ORGANISM: Artificial Sequence
<220> FEATURE:
<223> OTHER INFORMATION: synthetic main immunogenic region (MIR) peptide
<220> FEATURE:
<221> NAME/KEY: MISC_FEATURE
<222> LOCATION: (10)..(10)
<223> OTHER INFORMATION: Xaa is any amino acid; preferably Xaa is Asn or Lys
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(112)
<223> OTHER INFORMATION: Xaa is any amino acid; Xaa may be present or absent
<220> FEATURE:
<221> NAME/KEY: MISC_FEATURE
<222> LOCATION: (118)..(118)
<223> OTHER INFORMATION: Xaa is any amino acid; preferably Xaa is Ala or Asp
<220> FEATURE:
<221> NAME/KEY: MISC_FEATURE
<222> LOCATION: (123)..(123)
<223> OTHER INFORMATION: Xaa is any amino acid; preferably Xaa is Ile or Val
<220> FEATURE:
<221> NAME/KEY: MISC_FEATURE
<222> LOCATION: (128)..(128)
<223> OTHER INFORMATION: Xaa is any amino acid
<220> FEATURE:
<221> NAME/KEY: MISC_FEATURE
<222> LOCATION: (129)..(227)
<223> OTHER INFORMATION: Xaa is any amino acid; Xaa may be present or absent
<220> FEATURE:
<221> NAME/KEY: MISC_FEATURE
<222> LOCATION: (229)..(229)
<223> OTHER INFORMATION: Xaa is any amino acid; preferably Xaa is Asp or Gln

<400> SEQUENCE: 31

Ser Glu His Glu Thr Arg Leu Val Ala Xaa Leu Phe Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Xaa Xaa Xaa
65 70 75 80

Xaa Xaa Xaa Xaa Xaa Xaa Xaa Xaa Xaa Xaa Xaa Xaa Xaa Xaa Xaa Xaa
85 90 95

-continued

```
Xaa Xaa Xaa Xaa Xaa Xaa Xaa Xaa Xaa Xaa Xaa Xaa Xaa Xaa Xaa Xaa
            100                 105                 110

Leu Lys Trp Asn Pro Xaa Asp Tyr Gly Gly Xaa Lys Lys Ile His Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Leu Xaa Tyr Thr Gly His
225                 230


<210> SEQ ID NO 32
<211> LENGTH: 4
<212> TYPE: PRT
<213> ORGANISM: Artificial Sequence
<220> FEATURE:
<223> OTHER INFORMATION: synthetic linker peptide

<400> SEQUENCE: 32

Gly Gly Gly Ser
1
```